(12) United States Patent
Sakurai et al.

(10) Patent No.: US 10,751,005 B2
(45) Date of Patent: Aug. 25, 2020

(54) VITAL INFORMATION MONITOR

(71) Applicant: NIHON KOHDEN CORPORATION, Tokyo (JP)

(72) Inventors: Teruko Sakurai, Tokyo (JP); Hiroshi Kubo, Tokyo (JP); Akira Nobukuni, Tokyo (JP); Shingo Wake, Tokyo (JP); Rie Muneshima, Tokyo (JP); Tomoko Goto, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 255 days.

(21) Appl. No.: 15/566,871

(22) PCT Filed: Apr. 8, 2016

(86) PCT No.: PCT/JP2016/061530
§ 371 (c)(1),
(2) Date: Oct. 16, 2017

(87) PCT Pub. No.: WO2016/167192
PCT Pub. Date: Oct. 20, 2016

(65) Prior Publication Data
US 2018/0132798 A1 May 17, 2018

(30) Foreign Application Priority Data
Apr. 17, 2015 (JP) .................. 2015-085133

(51) Int. Cl.
*A61B 5/00* (2006.01)
*A61M 16/01* (2006.01)
(Continued)

(52) U.S. Cl.
CPC ............... *A61B 5/742* (2013.01); *A61B 5/00* (2013.01); *A61B 5/024* (2013.01); *A61B 5/0452* (2013.01);
(Continued)

(58) Field of Classification Search
None
See application file for complete search history.

(56) References Cited

U.S. PATENT DOCUMENTS

2002/0099571 A1 7/2002 Waku et al.
2003/0135087 A1 7/2003 Hickle et al.
(Continued)

FOREIGN PATENT DOCUMENTS

CN 1610516 A 4/2005
CN 103893866 A 7/2014
(Continued)

OTHER PUBLICATIONS

Extended European Search Report dated Nov. 14, 2018 issued by the European Patent Office in Counterpart European Application No. 16779983.2.
(Continued)

*Primary Examiner* — Eric F Winakur
*Assistant Examiner* — Marjan Fardanesh
(74) *Attorney, Agent, or Firm* — Sughrue Mion, PLLC

(57) ABSTRACT

A vital information monitor (1) includes a vital sign acquiring section (39) which acquires vital signs of a patient into whom a tracheal tube (14) connected to a respirator (13) is intubated, a producing section (31) which produces an extubation process display screen (72) on which determination items contained in an extubation process for removing the tracheal tube (14) from the patient are displayed, a displaying section (7) on which the vital signs acquired by the vital sign acquiring section and the extubation process display screen (72) are displayed, and a determining section (30) which determines whether the determination items satisfy predetermined conditions.

12 Claims, 23 Drawing Sheets

(51) Int. Cl.
*A61M 16/04* (2006.01)
*A61B 5/08* (2006.01)
*A61B 5/0452* (2006.01)
*A61M 16/00* (2006.01)
*A61B 5/024* (2006.01)

(52) U.S. Cl.
CPC .......... *A61B 5/0816* (2013.01); *A61B 5/4836* (2013.01); *A61B 5/7275* (2013.01); *A61M 16/0051* (2013.01); *A61M 16/04* (2013.01); *A61B 5/4821* (2013.01); *A61M 2205/3553* (2013.01); *A61M 2205/3561* (2013.01); *A61M 2205/3584* (2013.01); *A61M 2205/3592* (2013.01); *A61M 2205/52* (2013.01); *A61M 2205/584* (2013.01); *A61M 2230/06* (2013.01); *A61M 2230/30* (2013.01); *A61M 2230/42* (2013.01)

(56) References Cited

U.S. PATENT DOCUMENTS

| | | |
|---|---|---|
| 2005/0267337 A1 | 12/2005 | Sakai et al. |
| 2011/0041850 A1 | 2/2011 | Vandine et al. |
| 2012/0041279 A1 | 2/2012 | Freeman et al. |
| 2013/0006075 A1 | 1/2013 | Baker, Jr. et al. |
| 2013/0023781 A1 | 1/2013 | Freeman et al. |
| 2013/0199534 A1 | 8/2013 | Steinhauer et al. |
| 2014/0060541 A1 | 3/2014 | Boyer et al. |
| 2014/0150796 A1 | 6/2014 | Milne |
| 2014/0371543 A1 | 12/2014 | Steinhauer et al. |
| 2014/0371618 A1 | 12/2014 | Steinhauer et al. |
| 2016/0367186 A1 | 12/2016 | Freeman et al. |

FOREIGN PATENT DOCUMENTS

| | | |
|---|---|---|
| CN | 104399164 A | 3/2015 |
| JP | H 11-206884 A | 8/1999 |
| JP | 2002207824 A | 7/2002 |
| JP | 2005342028 A | 12/2005 |
| JP | 2014502854 A | 2/2014 |
| JP | 2016-521621 A | 7/2016 |
| WO | 2012/106270 A2 | 8/2012 |
| WO | 2014/063256 A1 | 5/2014 |

OTHER PUBLICATIONS

International Search Report dated Jun. 28, 2016, issued by the International Searching Authority in counterpart International Application No. PCT/JP2016/061530 (PCT/ISA/210).
Written Opinion dated Jun. 28, 2016, issued by the International Searching Authority in counterpart International Application No. PCT/JP2016/061530 (PCT/ISA/237).
Communication dated Aug. 28, 2018, issued by the Japanese Patent Office in counterpart Japanese Patent Application No. 2015-085133.
Communication dated Dec. 27, 2019 issued by the State Intellectual Property Office of P.R. China in counterpart Chinese Application No. 201680022430.0.
"Critical Care Training Toolkit", World Health Organization(WHO), May 2014, pp. 83-86, 11 pages total.

SAT EXECUTION DETERMINATION PROCESS

COLOR DISPLAY CHANGING PROCESS

AUTOMATIC DETERMINATION PROCESS

MANUAL DETERMINATION PROCESS

DETERMINATION RESULT REWRITING PROCESS

FIG. 19

| SAT EXECUTION DETERMI-NATION | SAT EXECUTION | SBT EXECUTION DETERMI-NATION | SBT EXECUTION | EXTUBATION PROTOCOL |

EVALUATION OF POST-EXTUBATION AIRWAY OBSTRUCTION

EVALUATION OF RISK OF REINTUBATION

EVALUATION OF POST-EXTUBATION AIRWAY OBSTRUCTION

- LONG-TERM INTUBATION ☑
- FEMALE ☑
- LARGE DIAMETER TRACHEAL TUBE ☑
- TRAUMATIC CASE ☑

| CUFF-LEAK TEST | NECESSARY | UNNECESSARY |

| SAT EXECUTION DETERMINATION | SAT EXECUTION | SBT EXECUTION DETERMINATION | SBT EXECUTION | EXTUBATION PROTOCOL |
|---|---|---|---|---|

EVALUATION OF POST-EXTUBATION AIRWAY OBSTRUCTION

EVALUATION OF RISK OF REINTUBATION

DETERMINATION OF VERY HIGH-RISK GROUP

| AFTER SURGERY OF PHARYNX/ORAL CAVITY | APPLICABLE | NOT APPLICABLE |
| TRACHELEMATOMA: AFTER SURGERY | APPLICABLE | NOT APPLICABLE |
| POSSIBILITY OF RECURRENT NERVE PALSY | APPLICABLE | NOT APPLICABLE |
| TRISMUS | APPLICABLE | NOT APPLICABLE |
| AFTER SURGERY OF CERVICAL SPINE | APPLICABLE | NOT APPLICABLE |
| HISTORY OF DIFFICULT EXTUBATION | APPLICABLE | NOT APPLICABLE |
| POSITIVENESS OF CUFF-LEAK TEST | APPLICABLE | NOT APPLICABLE |
| VERY HIGH-RISK GROUP | APPLICABLE | NOT APPLICABLE |

FIG. 21

| SAT EXECUTION DETERMI- NATION | SAT EXECUTION | SBT EXECUTION DETERMI- NATION | SBT EXECUTION | POST- EXTUBATION VITAL |
|---|---|---|---|---|
| ELAPSED TIME PERIOD FROM EXTUBATION 40:35 ||||||
| 2012 | 06-24 13:30 | 06-24 13:45 | 06-24 14:00 | 06-24 14:15 |
| HR | 1 | 80 | 80 | 80 |
| RR | 12 | 11 | 15 | 12 |
| ART-S | 100 | 110 | 112 | 102 |
| ART-D | 50 | 55 | 50 | 55 |
| ART-M | 70 | 84 | 75 | 70 |
| SpO2 | 98 | 96 | 99 | 93 |
| CRITICAL CONDITION | ▨ | ▨ | ▨ | ▨ |
| LONG-TERM WAVEFORM | ▨ | ▨ | ▨ | ▨ |
| BLOOD GAS | 98 | 98 | INPUT | INPUT |
| COMMENT | INPUT | INPUT | INPUT | INPUT |

HR 80 (140 / 80)
SpO2 98 (98 / 95)
RR 15 (20 / 10)
CO2 35 (40 / 30)

13:30  13:45  14:00  14:15

VITAL INFORMATION MONITOR

TECHNICAL FIELD

The present invention relates to a vital information monitor.

BACKGROUND ART

A series of processes for removing a tracheal tube, connected to a respirator, from the patient (hereinafter, referred to as an extubation process) are performed according to a subjective determination based on an experience of a doctor. In this way, determination criteria for the extubation process varies depending each doctor, and hence there occurs a situation where, after the extubation process, the tracheal tube of the respirator is again intubated into the patient. In order to prevent such a situation, extubation protocols defining determination criteria and sequences of an extubation process are stipulated in an academic society and in each hospital.

Patent Document 1 discloses a respirator in which a weaning operation (extubation process) is automated in accordance with certain determination criteria. Patent Document 1 discloses performing a certain processing based on vital signs (vital information) obtained from the respirator and fuzzy logic, thereby automating the weaning operation.

PRIOR ART DOCUMENT

Patent Document

Patent Document 1: JPH11-206884A

SUMMARY OF INVENTION

Problem to be Solved by Invention

In the respirator disclosed in Patent Document 1, however, the weaning operation is performed based on only vital signs obtained from the respirator. Therefore, vital signs required by the extubation protocols published by an academic society or the like cannot be sufficiently obtained, and the weaning operation cannot be performed based on the extubation protocols. In order to perform the weaning operation based on the extubation protocol, a manual determination is necessary, and therefore this imposes a burden on a medical person.

It is an object of the invention to provide a vital information monitor which can reduce a burden on a medical person who performs an extubation process based on determination items.

Means for Solving the Problem

A vital information monitor according to an aspect of the present invention includes a vital sign acquiring section which acquires vital signs of a patient into whom a tracheal tube connected to a respirator is intubated, a producing section which produces an extubation process display screen on which determination items contained in an extubation process for removing the tracheal tube from the patient are displayed, a displaying section on which the vital signs acquired by the vital sign acquiring section and the extubation process display screen are displayed, and a determining section which determines whether the determination items satisfy predetermined conditions.

According to the present invention, it is possible to provide a vital information monitor which can reduce a burden on a medical person who performs an extubation process based on the determination items.

BRIEF DESCRIPTION OF THE DRAWINGS

FIG. 19 illustrates an extubation process display screen for a post-extubation monitoring step on which evaluation items of post-extubation airway obstruction are displayed.

FIG. 20 illustrates the extubation process display screen for the post-extubation monitoring step on which very high-risk group determination items are displayed.

FIG. 21 illustrates the extubation process display screen for the post-extubation monitoring step on which vital signs of a post-extubation patient are displayed.

EMBODIMENTS OF INVENTION

Figure 1:
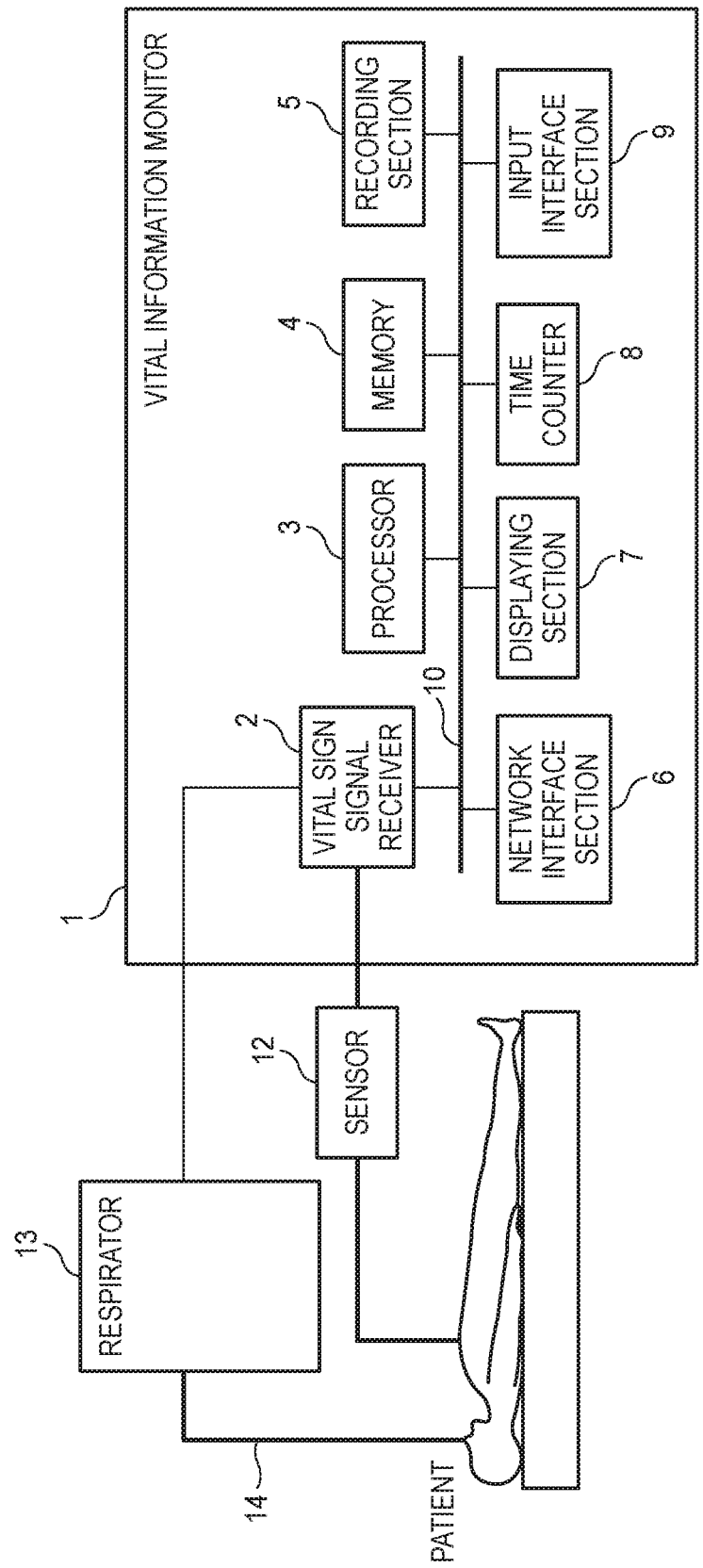
FIG. 1 is a hardware configuration diagram of a vital information monitor according to an embodiment of the present invention.

Hereinafter, an embodiment of the present invention will be described with reference to the drawings. In the following description of the embodiment, the description of components denoted by the same reference numerals as the components that have already been described will be omitted for the sake of convenience of description.

FIG. 1 is a hardware configuration diagram of a vital information monitor 1 of the embodiment. As shown in FIG. 1, a tracheal tube 14 connected to a respirator 13 is intubated into the patient. The breathing of the patient is assisted by the respirator 13 through the tracheal tube 14. A sensor 12 is attached to the patient, and configured so as to acquire a vital sign signal of the patient. The vital information monitor 1 is connected to the respirator 13 and the sensor 12.

For example, the vital information monitor 1 is a bedside monitor, and includes a vital sign signal receiver 2, a processor 3, a memory 4, a recording section 5, a network interface section 6, a displaying section 7, a time counter 8, and an input interface section 9. These components are communicably connected to one another through a bus 10.

The vital sign signal receiver 2 is communicably connected to the respirator 13 and the sensor 12, and configured so as to receive vital sign signals acquired by the respirator 13 and the sensor 12, respectively. The memory 4 includes a nonvolatile memory such as a ROM (Read Only Memory) which stores various programs and the like, and a volatile memory such as a RAM (Random Access Memory) having a plurality of work areas in which various programs and the like to be executed by the processor 3 are to be stored. The processor 3 is configured so as to expand designated one of the various programs stored in the ROM, on the RAM, and cooperate with the RAM to execute various processes.

The recording section 5 is configured so as to record history information such as determination items, determination results, and patient information which will be described later. For example, the recording section 5 is a memory card, a hard disk drive, or a flash memory. The network interface section 6 is configured so as to enable the vital information monitor 1 to be connectable to a communication network such as a LAN (Local Area Network) or the Internet. For example, the history information is transmitted to a host computer which is placed on the LAN through the network interface section 6.

The displaying section 7 is a display device which is configured so as to display a vital sign screen and extubation process display screen that will be described later, and which is incorporated in the housing of the vital information monitor 1, or disposed separately from the housing. The input interface section 9 is configured so as to receive an input operation of the operator who operates the vital information monitor 1, and is a touch display which is placed on, for example, the displaying section 7, a keyboard, a mouse, or the like.

Figure 2:
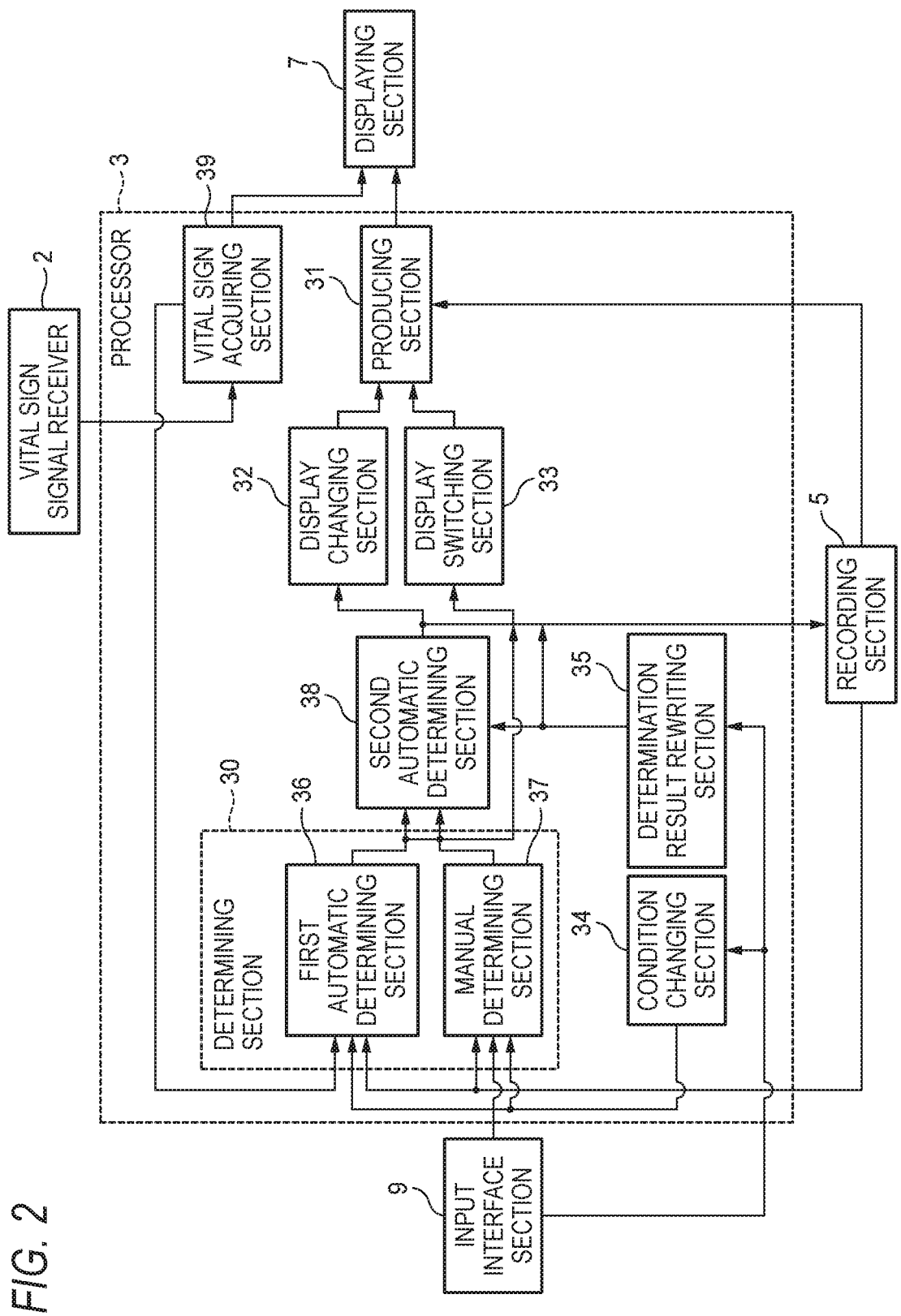
FIG. 2 is a functional block diagram of the vital information monitor of the embodiment.

FIG. 2 is a functional block diagram of the vital information monitor 1 of the embodiment. As shown in FIG. 2, the processor 3 includes a determining section 30, a producing section 31, a display changing section 32, a display switching section 33, a condition changing section 34, a determination result rewriting section 35, a second automatic determining section 38, and a vital sign acquiring section 39. The determining section 30 includes a first automatic determining section 36 and a manual determining section 37. The processor 3 reads out various programs from the memory 4, and temporarily stores calculation results in the memory 4 or a register of the processor, and therefore functions as the above-described components. The components will be described later in detail.

Figure 3:
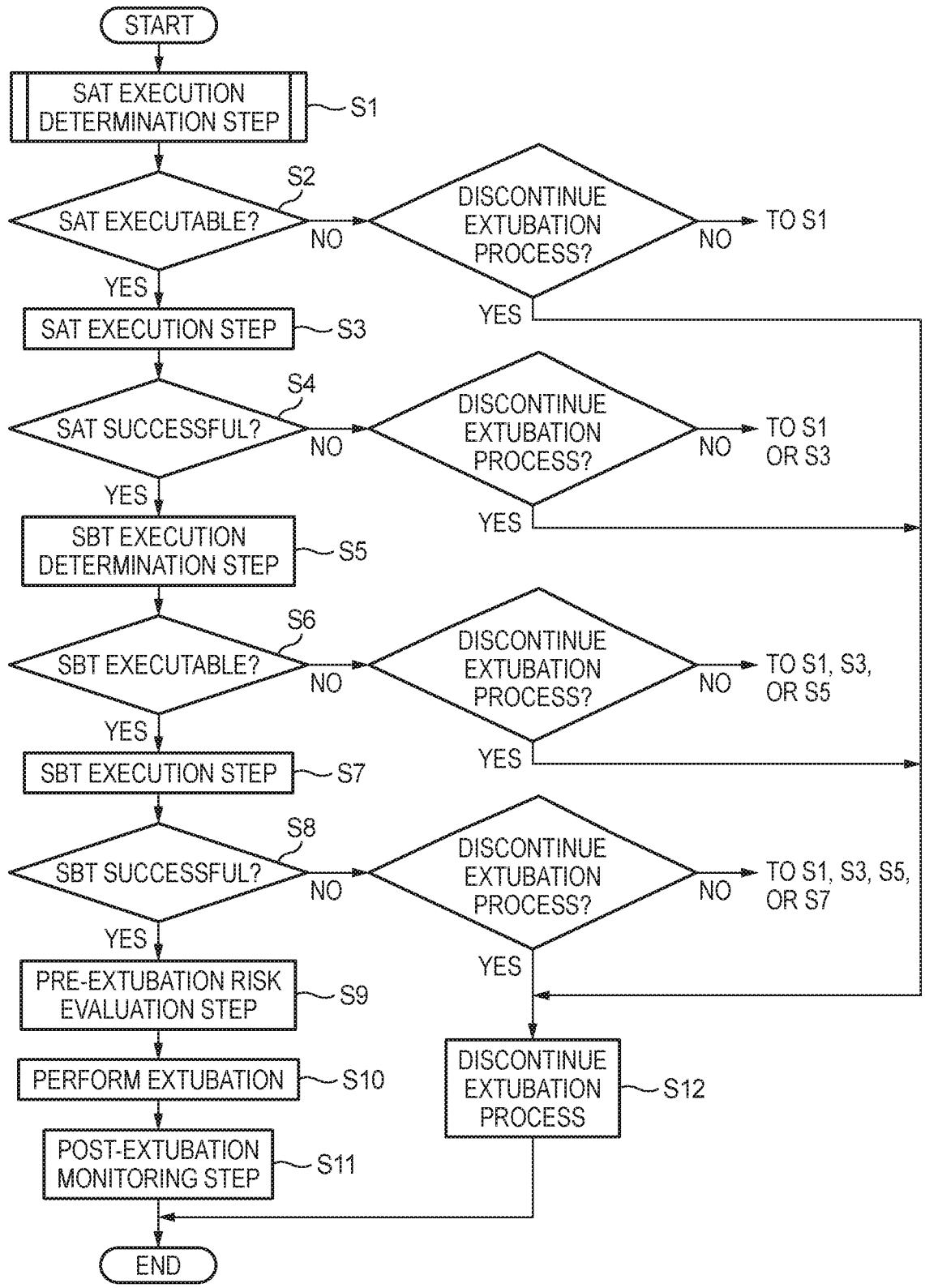
FIG. 3 is a flowchart illustrating an extubation process.

FIG. 3 is a flowchart illustrating the extubation process which is a series of processes of removing the tracheal tube connected to the respirator, from the patient. As shown in FIG. 3, the extubation process is configured by a plurality of steps, and mainly includes an SAT (Spontaneous Awakening Trial) execution determination step (S1), an SAT execution step (S3), an SBT (Spontaneous Breathing Trial) execution determination step (S5), and an SBT execution step (S7).

The SAT execution determination step is a step of determining whether administration of a sedative in the patient can be discontinued or not, or whether the amount of a sedative to be administered to the patient can be reduced or not. The SAT execution step is a step of evaluating whether or not the awakening of the patient is attained in the state where administration of the sedative in the patient is discontinued, or where the amount of the sedative to be administered to the patient is reduced.

The SBT execution determination step is a step of determining whether or not the state can be transferred to a support minimum state where at least support by the respirator for breathing of the patient is minimum, or an unsupported state where support by the respirator for breathing of the patient is not performed. The SBT execution step is a step of evaluating spontaneous breathing of the patient in the support minimum state or the unsupported state.

Figure 4:
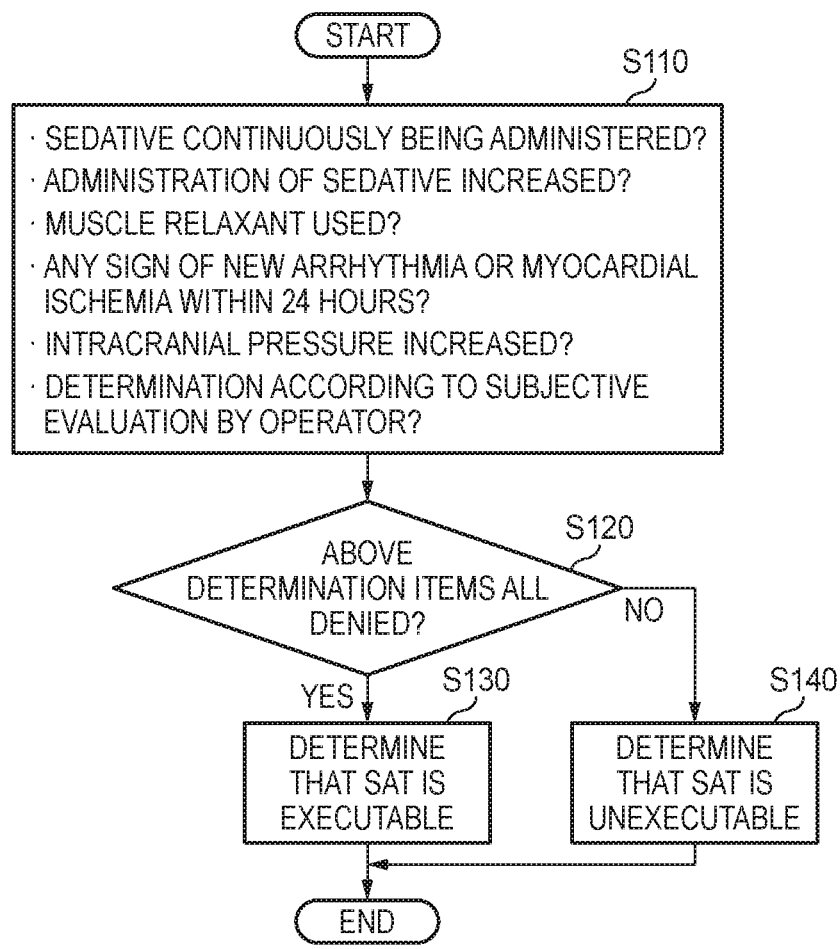
FIG. 4 is a flowchart illustrating an SAT execution determination step.

Each of the above-described steps has a plurality of determination items. For example, the SAT execution determination step (S1) will be described with reference to FIG. 4. As shown in FIG. 4, the SAT execution determination step has, for example, the following determination items. These determination items may contain an automatic determination item which is automatically determined by the vital information monitor 1, and a manual determination item which is determined in accordance with an input operation of the operator. The automatic determination item and the manual determination item will be described later.

Whether a sedative is being continuously administered
Whether administration of a sedative has been increased
Whether a muscle relaxant has been used
Whether there is a sign of new arrhythmia or myocardial ischemia within 24 hours
Whether the intracranial pressure is increased
Determination according to a subjective evaluation by an operator such as a doctor (specifically, determination according to a subjective evaluation as to whether SAT is executable)

As apparent from the flowchart of FIG. 4, all of the above-described determination items are determined (S110). As a result, if the situation does not correspond to all of the determination items (Yes in S120), it is determined that SAT is executable (S130). By contrast, if the situation corresponds to one of the determination items (No in S120), it is determined that SAT is unexecutable (S140). The determination items of the SAT execution determination step shown in FIG. 4 are mere examples.

Returning to the flowchart of FIG. 3, the description will be made. If, as a result of the SAT execution determination step, it is determined that SAT is executable (Yes in S2), the process proceeds to the SAT execution step (S3). By contrast, if it is determined that SAT is unexecutable (No in S2), the process returns to the SAT execution determination step (S1), or the extubation process is discontinued (S12).

While the SAT execution step (S3) has been summarized above, the step has the following determination items as specific examples:

Is the RASS scale from −1 to 0

Does any problem occur with the patient after elapse of 30 minutes or longer from discontinuance of administration of a sedative in the patient If, as a result of the SAT execution step, SAT succeeds (Yes in S4), the process proceeds to the SBT execution determination step (S5). By contrast, if SAT fails (No in S4), the process returns to a step preceding the SAT execution step, or the extubation process is discontinued (S12).

While the SBT execution determination step (S4) has been summarized above, the step has the following determination items as specific examples:

Whether oxygenation is sufficient

Whether hemodynamics is stable

Whether sufficient spontaneous breathing is sufficient

Whether there is no abnormal breathing pattern

Whether general status of the patient is stable

If, as a result of the SBT execution determination step, it is determined that SBT is executable (Yes in S6), the process proceeds to the SBT execution step (S7). By contrast, if it is determined that SBT is unexecutable (No in S6), the process returns to a step preceding the SBT execution determination step, or the extubation process is discontinued (S12).

While the SBT execution step (S7) has been summarized above, the step has the following determination items as specific examples:

Whether the respiration rate (RR), the SpO2, the PaO2, and the heart rate satisfy predetermined values Whether there is a sign of new arrhythmia or myocardial ischemia Whether there is a sign of tachypnea If, as a result of the SBT execution step, SBT succeeds (Yes in S8), the process proceeds to an extubation risk pre-evaluation step (S9). By contrast, if SBT fails (No in S8), the extubation process is discontinued (S12).

In the pre-extubation risk evaluation step (S9), before the tracheal tube 14 is pulled out from the patient, a risk associated with extubation is evaluated based on various items. After the pre-extubation risk evaluation step, the tracheal tube 14 is extubated out from the patient (S10). Thereafter, the extubated patient is monitored (S11), whereby the series of extubation processes is ended. In the step of monitoring the extubated patient (S11), for example, vital signs of the extubated patient are monitored. A step of evaluating the possibility of an airway obstruction in the extubated patient, and that of evaluating the possibility of reintubation of the tracheal tube 14 into the patient may be disposed prior to the monitoring step. The extubation process shown in FIG. 3 is a mere example, and various extubation processes may be set depending on hospitals.

Figure 5:
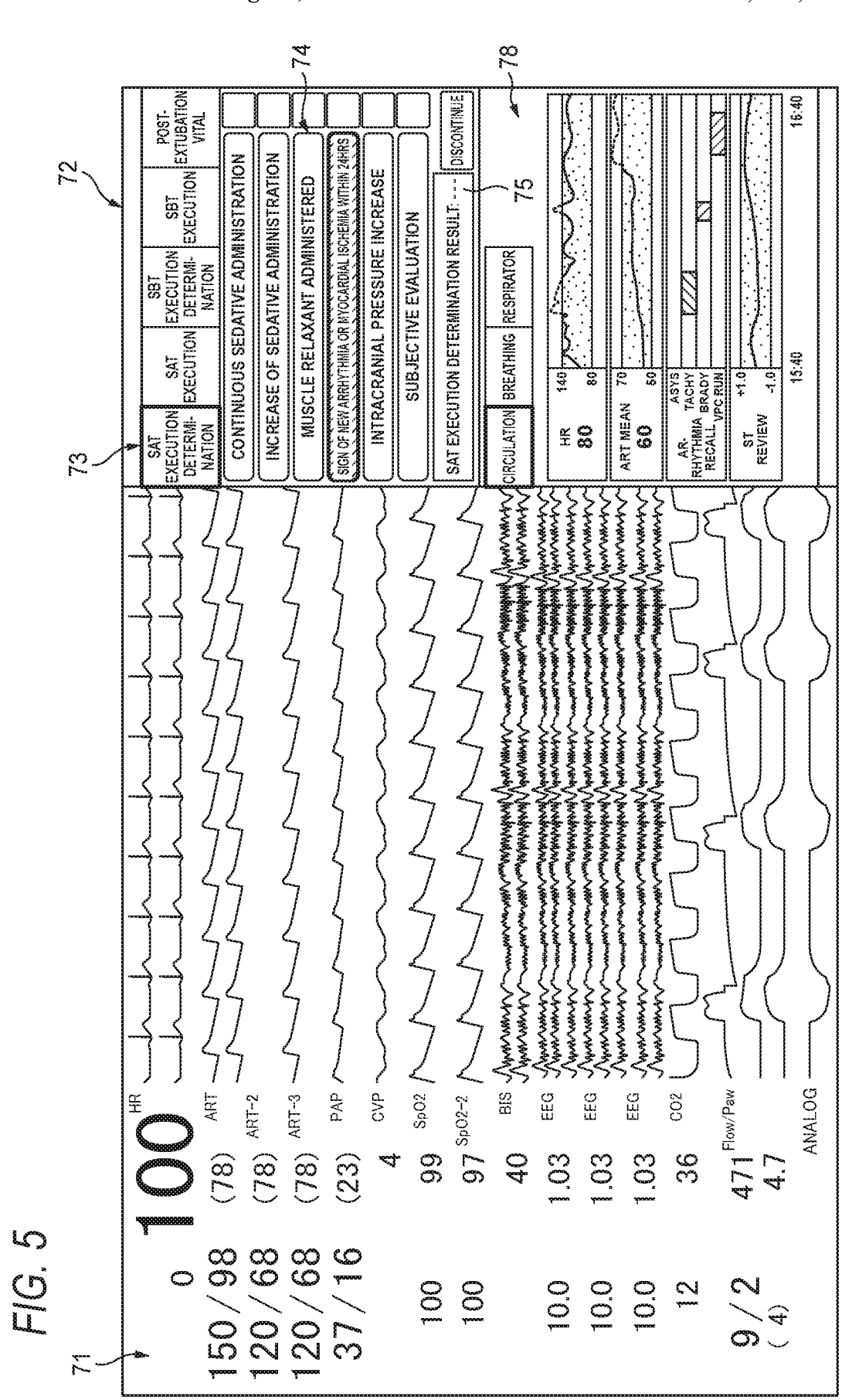
FIG. 5 illustrates a vital sign screen and an extubation process display screen displayed on a displaying section of the vital information monitor of the embodiment.

Next, a vital sign screen 71 and extubation process display screen 72 which are displayed on the displaying section 7 of the vital information monitor 1 of the embodiment will be described with reference to FIGS. 2 and 5. In the following description, the configurations shown in FIG. 2 will be appropriately mentioned. As shown in FIG. 5, the vital sign screen 71 and the extubation process display screen 72 are displayed on the displaying section 7. The extubation process display screen 72 is displayed in the right side of the displaying section 7 so as not to completely cover the vital sign screen 71. The plurality of determination items contained in the extubation process are displayed on the extubation process display screen 72. While the extubation process display screen 72 is displayed in the right side of the displaying section 7 in FIG. 5, the extubation process display screen 71 may be displayed in the lower side of the displaying section 7, and its display position can be arbitrarily changed. Moreover, the extubation process display screen 71 can be adequately minimized in accordance with an input operation of the operator. The extubation process display screen 72 may be displayed while partly overlapping with a display region where the vital sign screen 71 is displayed, or while completely not overlapping with the display region where the vital sign screen 71 is displayed. In the case where there are, for example, two displaying sections 7, the vital sign screen 71 may be displayed on one of the displaying sections 7, and the extubation process display screen 72 may be displayed on the other displaying section 7.

As shown in FIG. 2, the vital sign acquiring section 39 receives the vital sign signals of the patient which are supplied from the vital sign signal receiver 2, and performs a predetermined calculation process on the received vital sign signals, thereby acquiring the vital signs of the patient. The vital sings acquired by the vital sign acquiring section 39 are output to the displaying section 7. Here, the vital signs of the patient contain real-time waveforms, real-time data values, trend waveforms, and the like of the respiration rate, heart rate, mean arterial blood pressure, and the like of the patient. In the vital sign screen 71 shown in FIG. 5, real-time data values of the vital signs are displayed in the left end, and real-time waveforms of the vital signs are displayed in a middle portion.

The producing section 31 produces the extubation process display screen 72 based on information of the determination items and the like recorded in the recording section 5. The extubation process display screen 72 has: a step display region 73 where a plurality of steps included in the extubation process are to be displayed in juxtaposition; a determination item display region 74 where a plurality of determination items contained in each step are to be displayed in juxtaposition; a step determination result display region 75 where a determination result of the current step is to be displayed; and a vital sign display region 78.

Figure 6:
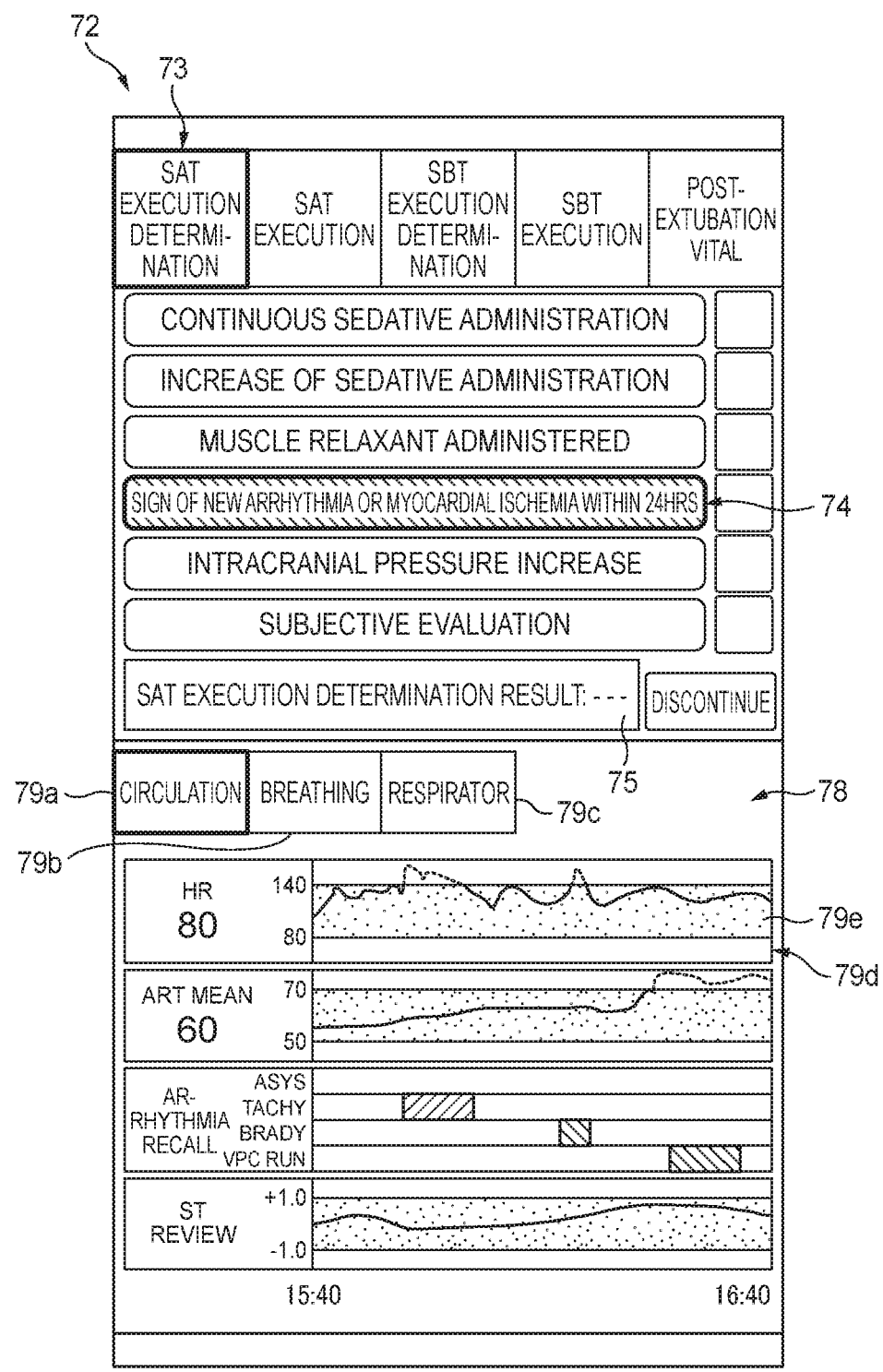
FIG. 6 illustrates an extubation process display screen for the SAT execution determination step.

The extubation process display screen 72 will be described in detail with reference to FIGS. 2 and 6. In the subsequent drawings, unless required in description, only the extubation process display screen 72 is illustrated, and the illustration of the vital sign screen 71 is omitted. FIG. 6 shows the extubation process display screen 72 for the SAT execution determination step.

As shown in FIG. 6, parts (the SAT execution determination step, the SAT execution step, the SBT execution determination step, the SBT execution step, and a post-extubation vital step (a part of a post-extubation monitoring step)) of the plurality of steps of the extubation process shown in FIG. 3 are displayed in juxtaposition in the step display region 73. In order to enable the operator to easily know the step which is currently performed, the mode of displaying the currently performed step may be differentiated from that of of displaying steps which are not currently performed. The SAT execution determination step is currently performed. In the figure, therefore, the SAT execution step may be displayed in a color which is different from the color of the other steps.

In the determination item display region 74, six determination items (see FIG. 4) contained in the SAT execution determination step are displayed in juxtaposition. The determination items of the respective steps are displayed in the determination item display region 74. In the case where the currently performed step is the SAT execution step, for example, determination items contained in the SAT execution step are displayed in juxtaposition in the determination item display region 74.

In the vital sign display region 78, trend waveforms (trend waveforms and the like of the mean arterial blood pressure (ART MEAN) and the heart rate (HR)) of partial vital signs which are acquired by the vital sign acquiring section 39.

In the left end of the vital sign display region 78, items 79a to 79c "CIRCULATION", "BREATHING" and "RESPIRATOR" are displayed in juxtaposition. When the operator designates the "CIRCULATION" item 79a, trend waveforms of vital signs relating to the circulation are displayed in the vital sign display region 78. When the operator designates the "BREATHING" item 79b, similarly, trend waveforms of vital signs relating to the breathing are displayed in the vital sign display region 78, and, when the operator designates the "RESPIRATOR" item 79c, trend waveforms of vital signs relating to the respirator are displayed in the vital sign display region 78.

Alternatively, an allowable range region may be displayed in the display region of trend waveforms displayed in the vital sign display region 78. As shown in FIG. 6, for example, an allowable range region 79e indicating an allowable range from 80 to 140 of the heart rate is displayed in an allowable range region 79d of the trend waveform of the heart rate (HR). In the case where a part of the trend waveform exceeds the allowable range region 79e, the display mode (for example, the display color) of the part of the trend waveform exceeding the allowable range region 79e may be changed. Therefore, the operator can easily know the trend of the heart rate.

As described above, while observing the trend waveforms displayed in the vital sign display region 78 of the extubation process display screen 72, the operator such as a medical person can perform determination of the items displayed in the determination item display region 74 of the extubation process display screen 72. In this way, the operability of the vital information monitor 1 is improved.

Next, the determining section 30 and the display changing section 32 will be described. The determining section 30 is configured so as to determine whether each determination item satisfies predetermined conditions. After the determination has been made on the determination item by the determining section 30, the display changing section 32 changes the display mode of the determined determination item. Particularly, the display changing section 32 changes the display color of the determination item in accordance with the determination result of the determination item. Here, "display color of the determination item" means the display color in the frame where the determination item is displayed.

Figure 7:
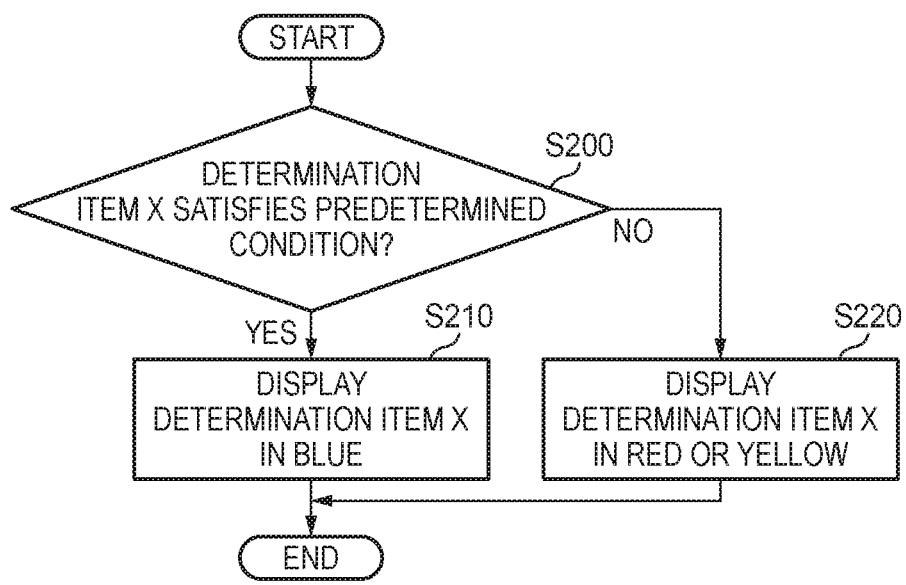
FIG. 7 is a flowchart illustrating a color display changing process of changing a display color of a determination item.

A color display changing process of changing the display color of a determination item will be described with reference to FIG. 7. FIG. 7 is a flowchart illustrating the color display changing process. In the determination process, the display color of a determination item on which determination has not yet been performed is set to, for example, gray. Before the determination process is started, namely, the display colors of all the determination items are gray. Firstly, the determining section 30 determines whether a determination item X satisfies predetermined conditions or not (S200). The kind of the determination item is not specified, and here the determination item is therefore designated as X.

If the determining section 30 determines that the determination item X satisfies the predetermined conditions (Yes in S200), the display changing section 32 changes the display color of the determination item X from gray to blue (S210).

By contrast, if the determining section 30 determines that the determination item X does not satisfy the predetermined conditions (No in S200), the display changing section 32 changes the display color of the determination item X from gray to red or yellow (S220). In the case where the determining section 30 determines that the determination item X slightly dissatisfies the predetermined conditions, for example, the display changing section 32 changes the display color of the determination item X from gray to yellow. On the other hand, in the case where the determining section 30 determines that the determination item X completely dissatisfies the predetermined conditions, the display changing section 32 changes the display color of the determination item X from gray to red. The above described pattern of display colors is an example, and the pattern may be adequately changed.

Figure 14:
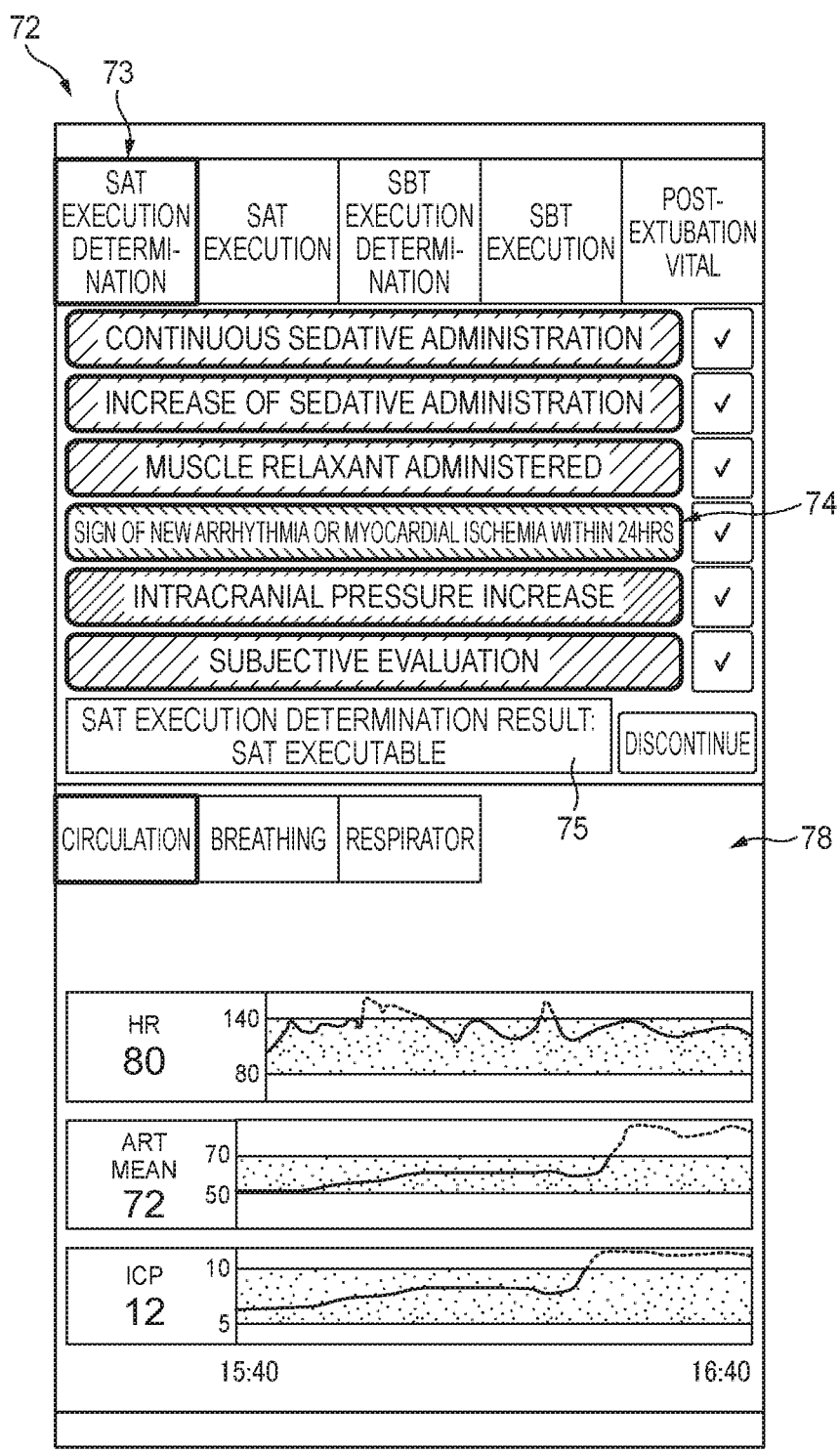
FIG. 14 illustrates the extubation process display screen for the SAT execution determination step on which determination results of the SAT execution determination step in which rewriting is performed by an input operation are displayed.

As shown in FIG. 6, the determination item "SIGN OF NEW ARRHYTHMIA OR MYOCARDIAL ISCHEMIA WITHIN 24 HRS" is displayed in yellow in accordance with the determination result. As shown in FIG. 14, moreover, each of the determination items of "CONTINUOUS SEDATIVE ADMINISTRATION", "INCREASE OF SEDATIVE ADMINISTRATION", "MUSCLE RELAXANT ADMINISTERED" and "SUBJECTIVE EVALUATION" is displayed in blue in accordance with the determination results, the determination item "INTRACRANIAL PRESSURE INCREASE" is displayed in red, and the determination item "SIGN OF NEW ARRHYTHMIA OR MYOCARDIAL ISCHEMIA WITHIN 24 HRS" is displayed in yellow.

Since the display modes of the determined determination items are changed as described, the operator can visually recognize determination items which have been already determined. Since the display colors of the determination items are changed in accordance with determination results, moreover, the operator can visually recognize which determination items satisfy the predetermined conditions or not. Therefore, it is possible to prevent an erroneous extubation process from being performed, and the operability of the vital information monitor 1 is improved.

Figure 8:
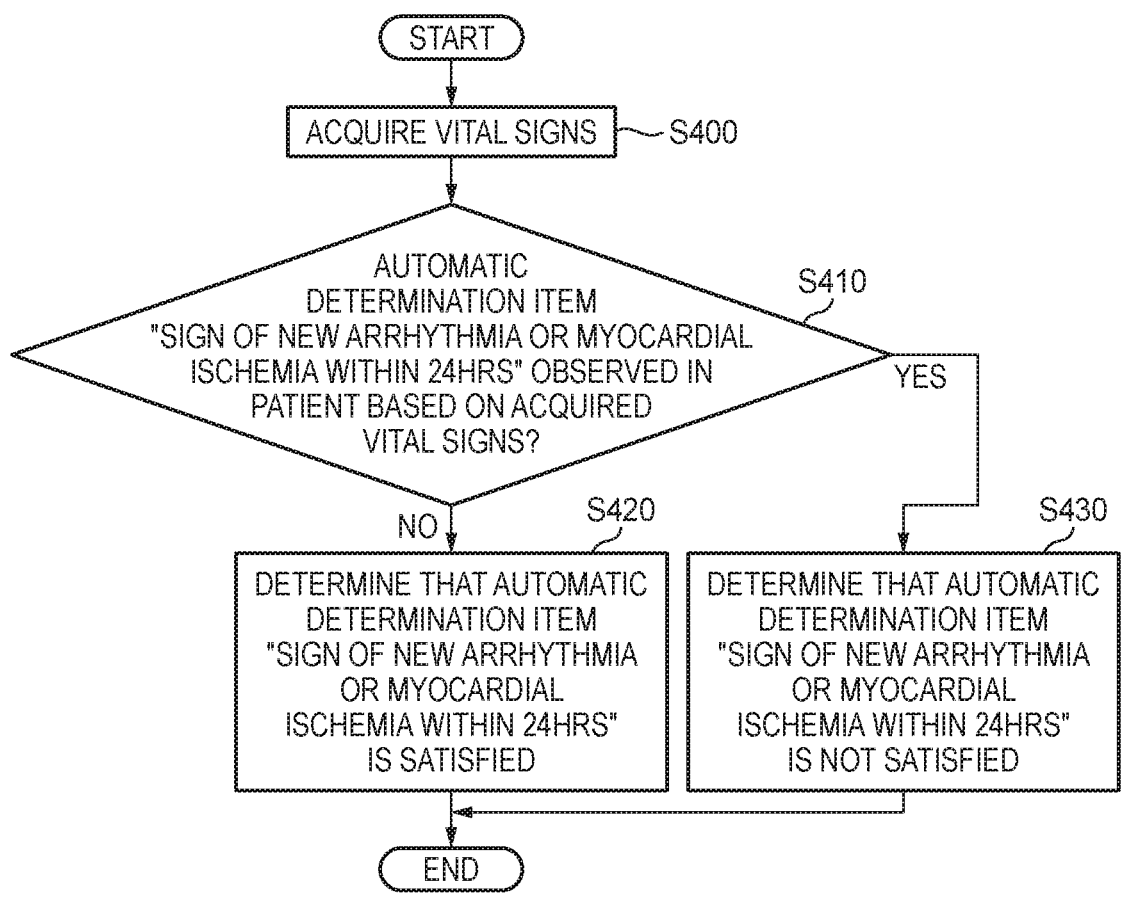
FIG. 8 is a flowchart illustrating an automatic determination process of determining an automatic determination item.

Next, an automatic determination process of determining an automatic determination item will be described with reference to FIGS. 2 and 8. FIG. 8 is a flowchart illustrating an automatic determination process of determining "SIGN OF NEW ARRHYTHMIA OR MYOCARDIAL ISCHEMIA WITHIN 24 HRS" which is an example of the automatic determination item.

The determination item has two kinds of determination items. Namely, the determination item has an automatic determination item which is to be automatically determined by the vital information monitor 1, and a manual determination item which is to be determined in response to an input operation of the operator. Among the six determination items shown in FIG. 6, for example, "SIGN OF NEW ARRHYTHMIA OR MYOCARDIAL ISCHEMIA WITHIN 24 HRS" may be set as an automatic determination item. The determination item which is set as an automatic determination item can be adequately changed, and, for example, the determination item "INTRACRANIAL PRESSURE INCREASE" may be set as an automatic determination item.

As shown in FIG. 2, the determining section 30 includes the first automatic determining section 36 and the manual determining section 37. The first automatic determining section 36 is configured so as to automatically determine whether an automatic determination item satisfies predetermined conditions or not, based on the vital signs acquired by the vital sign acquiring section 39. The manual determining section 37 is configured so as to determine whether a manual determination item satisfies predetermined conditions or not, in accordance with an input operation (a touch operation, a mouse operation, or the like) of the operator on the input interface section 9.

As shown in FIG. 8, initially, the vital sign acquiring section 39 acquires vital signs of the patient (S400). Next, the first automatic determining section 36 reads out the automatic determination item "SIGN OF NEW ARRHYTHMIA OR MYOCARDIAL ISCHEMIA WITHIN 24 HRS" from the recording section 5, and determines whether a sign of new arrhythmia or myocardial ischemia within 24 hours was observed in the patient or not, based on the vital signs acquired by the vital sign acquiring section 39 (S410). If such a sign was observed based on the vital signs (Yes in S410), the first automatic determining section 36 determines that the automatic determination item is not satisfied (S430). By contrast, if such a sign was not observed based on the vital signs (No in S410), the first automatic determining section 36 determines that the automatic determination item is satisfied (S420). As described above, the automatic determination process is executed by the first automatic determining section 36. Also other automatic determination items are determined by the first automatic determining section 36 with a technique similar to that of the flowchart shown in FIG. 8.

Figure 9:
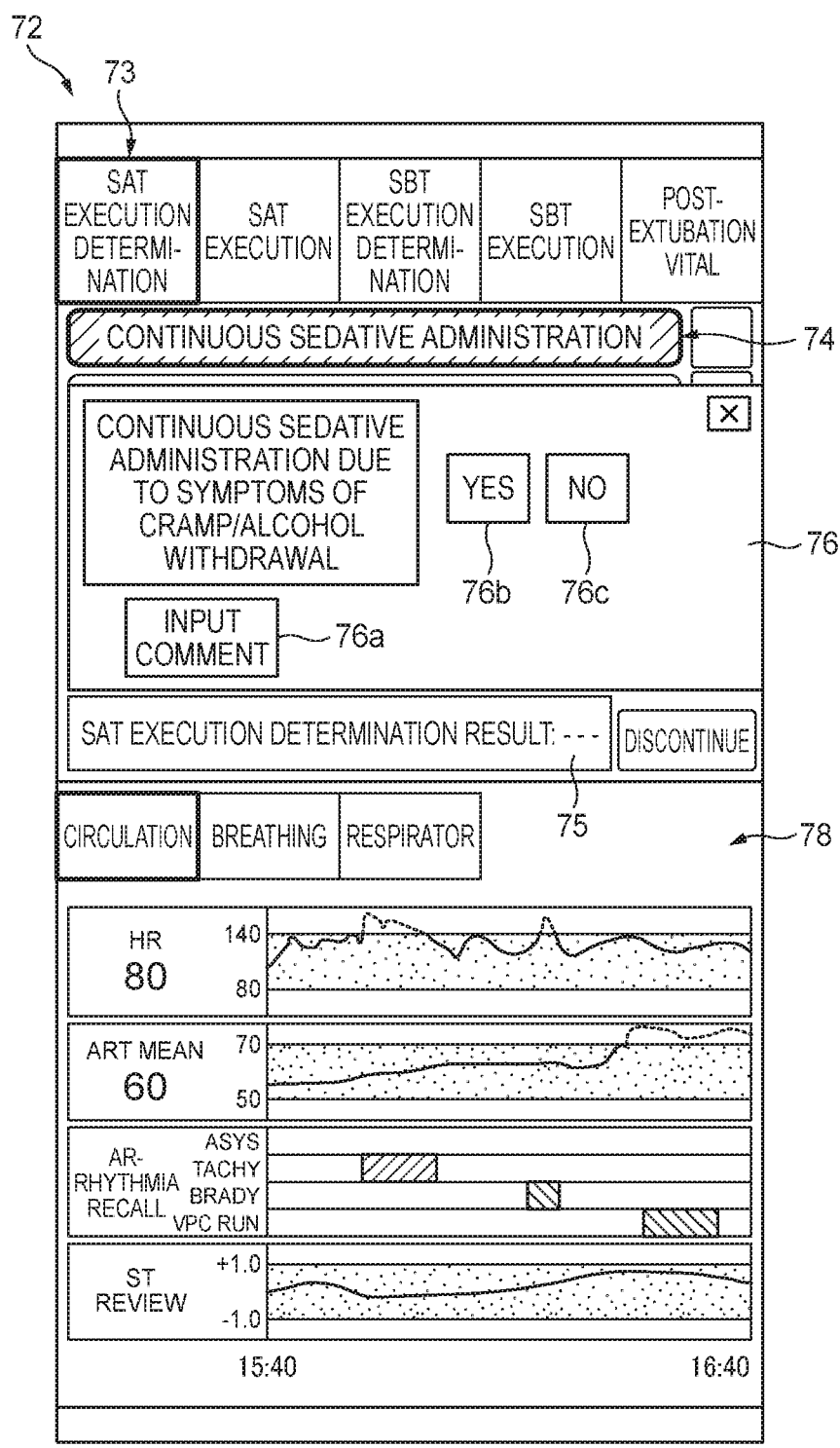
FIG. 9 illustrates the extubation process display screen for the SAT execution determination step on which an operation input screen for a manual determination item is displayed.
Figure 10:
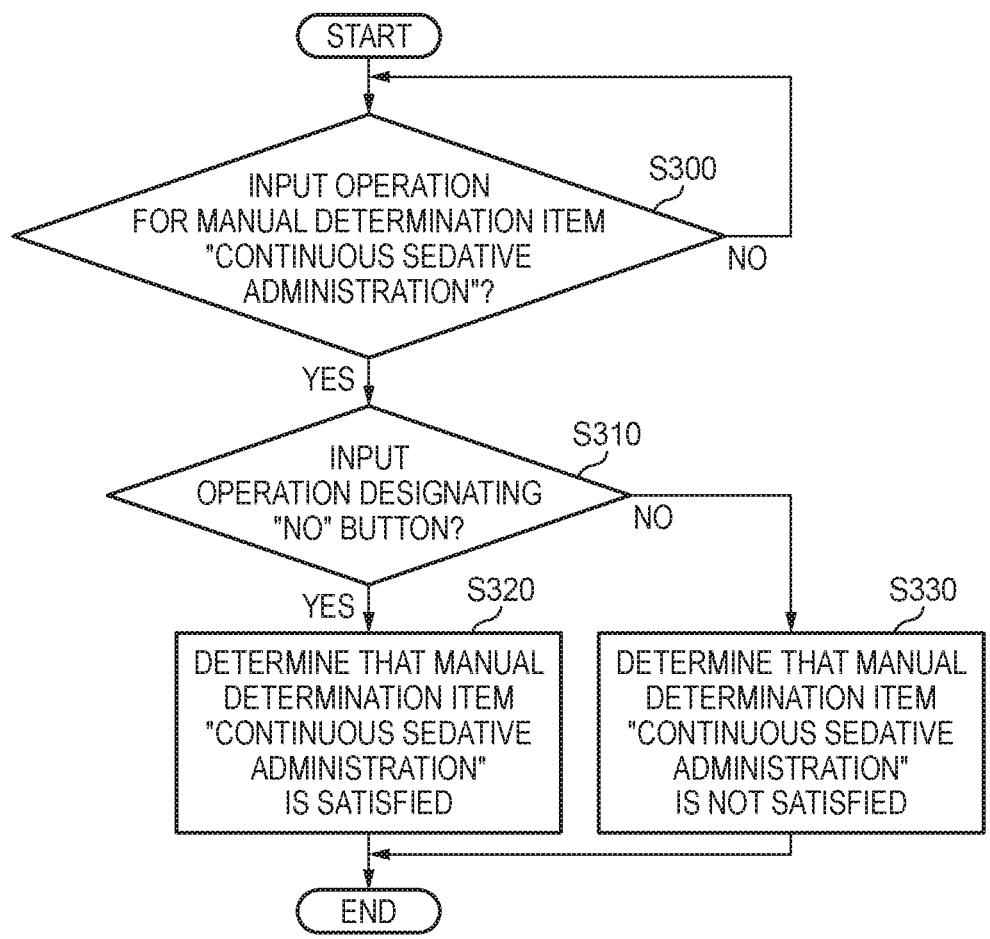
FIG. 10 is a flowchart illustrating a manual determination process of determining a manual determination item.
Figure 11:
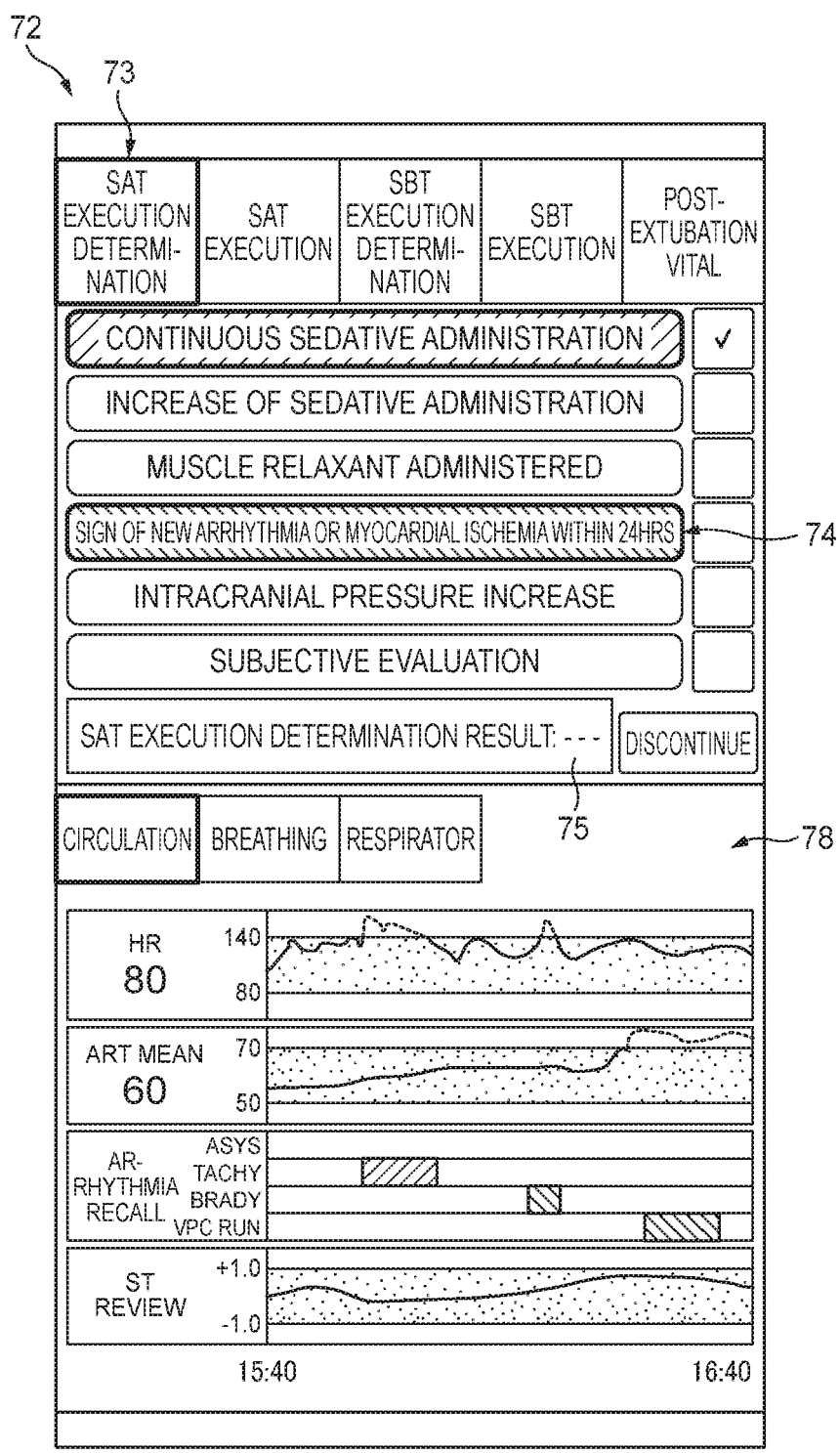
FIG. 11 illustrates the extubation process display screen for the SAT execution determination step on which determination results of two determination items are displayed.

Next, a manual determination process of determining a manual determination item will be described with reference to FIGS. 9 and 10. FIG. 9 shows the extubation process display screen 72 for the SAT execution determination step on which an operation input screen 76 for the manual determination item "CONTINUOUS SEDATIVE ADMINISTRATION" is displayed. An "INPUT COMMENT" button 76a, a "YES" button 76b, and a "NO" button 76c are displayed on the operation input screen 76. When the operator designates the "INPUT COMMENT" button 76a through the input interface section 9, a comment input column is displayed, and the operator can input information relating to the automatic determination item in the comment input column. The "YES" button 76b and the "NO" button 76c will be described with reference to FIG. 10. FIG. 10 is a flowchart illustrating a manual determination process of determining the manual determination item "CONTINUOUS SEDATIVE ADMINISTRATION".

As shown in FIG. 10, initially, the manual determining section 37 reads out the manual determination item "CONTINUOUS SEDATIVE ADMINISTRATION" from the recording section 5, and detects an input operation of the operator relating to the manual determination item through the input interface section 9 (S300). If the manual determining section 37 detects an input operation of the operator relating to the manual determination item (Yes in S300), the manual determining section 37 determines whether the input operation of the operator is an input operation of designating the "NO" button 76c, or that of designating the "YES" button 76b (S310). If the input operation is an input operation of designating the "NO" button 76c (Yes in S310), the manual determining section 37 determines that the manual determination item is satisfied (S320). By contrast, if the input operation is an input operation of designating the "YES" button 76b (No in S310), the manual determining section 37 determines that the manual determination item is not satisfied (S330). In this way, the manual determination process is executed by the manual determining section 37. Also other manual determination items are determined by the manual determining section 37 with a technique similar to that of the flowchart shown in FIG. 10.

As shown in FIG. 1, in accordance with determination results which are determined by the first automatic determining section 36 and the manual determining section 37, the display changing section 32 displays the automatic determination item "SIGN OF NEW ARRHYTHMIA OR MYOCARDIAL ISCHEMIA WITHIN 24 HRS" in yellow, and the manual determination item "CONTINUOUS SEDATIVE ADMINISTRATION" in blue.

According to the embodiment, it is possible to provide the vital information monitor 1 which can compatible with an extubation process containing a manual determination item that is to be manually determined based on the subjective view of the operator such as a medical person, and an automatic determination item that is to be automatically determined based on vital signs.

In the vital information monitor 1 of the embodiment, moreover, the operator can change the conditions of the determination items. As shown in FIG. 2, the condition changing section 34 is configured so as to change the conditions of the determination items in accordance with an input operation which is performed by the operator on the input interface section 9. For example, the condition changing section 34 changes various numerical conditions of vital signs for determining the automatic determination item "SIGN OF NEW ARRHYTHMIA OR MYOCARDIAL ISCHEMIA WITHIN 24 HRS" in accordance with an input operation which is performed by the operator on the input interface section 9. Since the conditions of the determination items can be changed by the medical person as described above, optimum determination items can be set according to the condition of the patient. Moreover, optimum determination items can be set according to the operational practice which is defined in each hospital.

Figure 12:
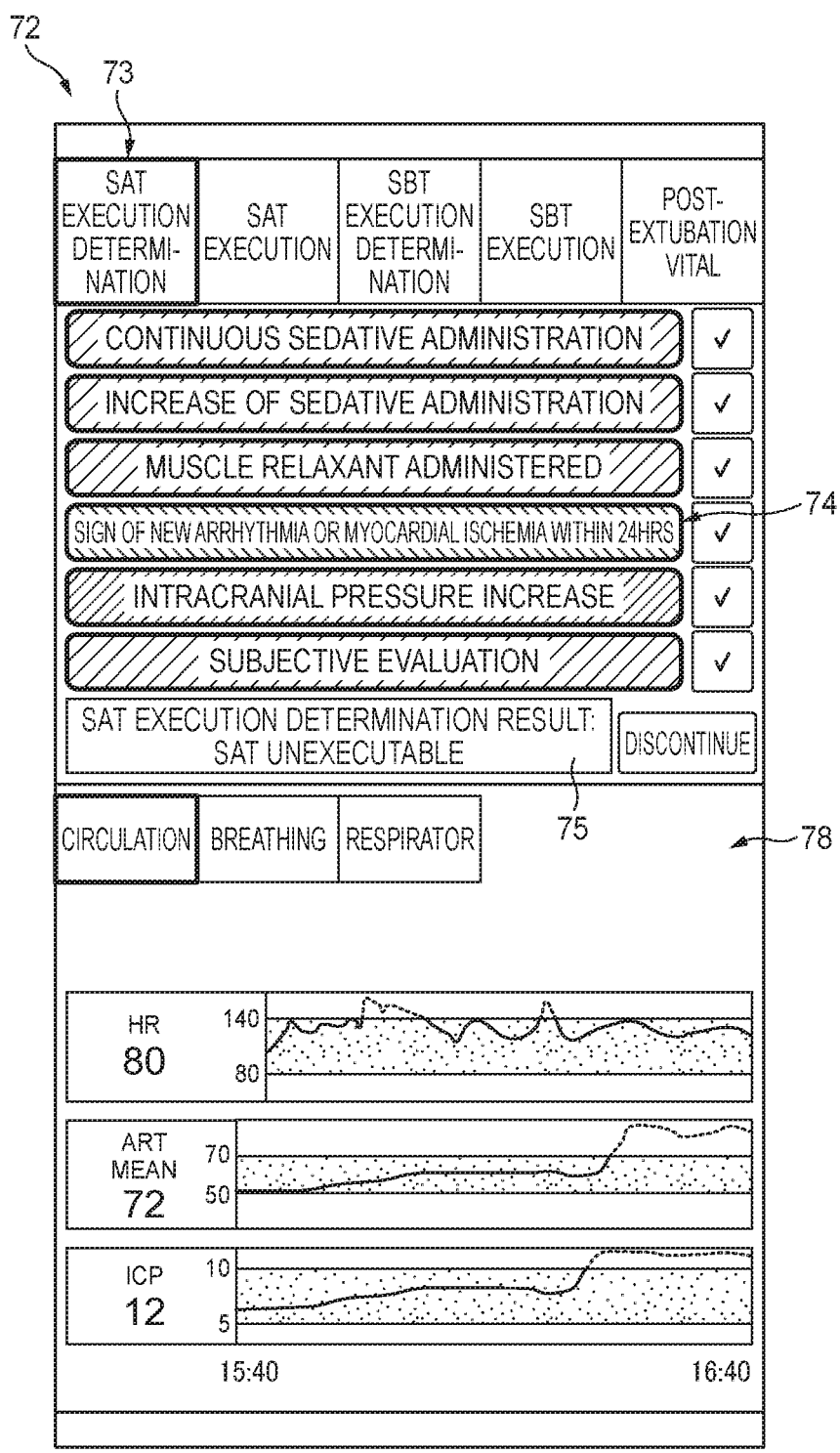
FIG. 12 illustrates the extubation process display screen for the SAT execution determination step on which determination results of the SAT execution determination step are displayed.

Next, determination results of the SAT execution determination step will be described with reference to FIG. 12. FIG. 12 shows the extubation process display screen 72 for the SAT execution determination step on which determination results of the SAT execution determination step are displayed. As above described with reference to the flowchart of FIG. 4, when all of the determination items of the SAT execution determination step are satisfied, it is determined that SAT is executable. By contrast, when even one of the determination items is not satisfied, it is determined that SAT is unexecutable.

As shown in FIG. 12, the determination item "SIGN OF NEW ARRHYTHMIA OR MYOCARDIAL ISCHEMIA WITHIN 24 HRS" is displayed in yellow, and the determination item "INTRACRANIAL PRESSURE INCREASE" is displayed in red. Therefore, the second automatic determining section 38 determines that SAT is unexecutable. Thereafter, the determination result of "SAT UNEXECUTABLE" which is determined by the second automatic determining section 38 is displayed in the step determination result display region 75. As described above, the second automatic determining section 38 is configured so as to automatically determine the success or failure of each step (the SAT execution determination step or the like) in accordance with determination results of a plurality of determination results of each step.

Since the success or failure of each step is automatically determined by the second automatic determining section 38, the operator can determine whether the process may proceed to the next step or not, based on the automatic determination.

In this way, it is possible to surely prevent an erroneous extubation process from being executed by the operator.

Figure 13:
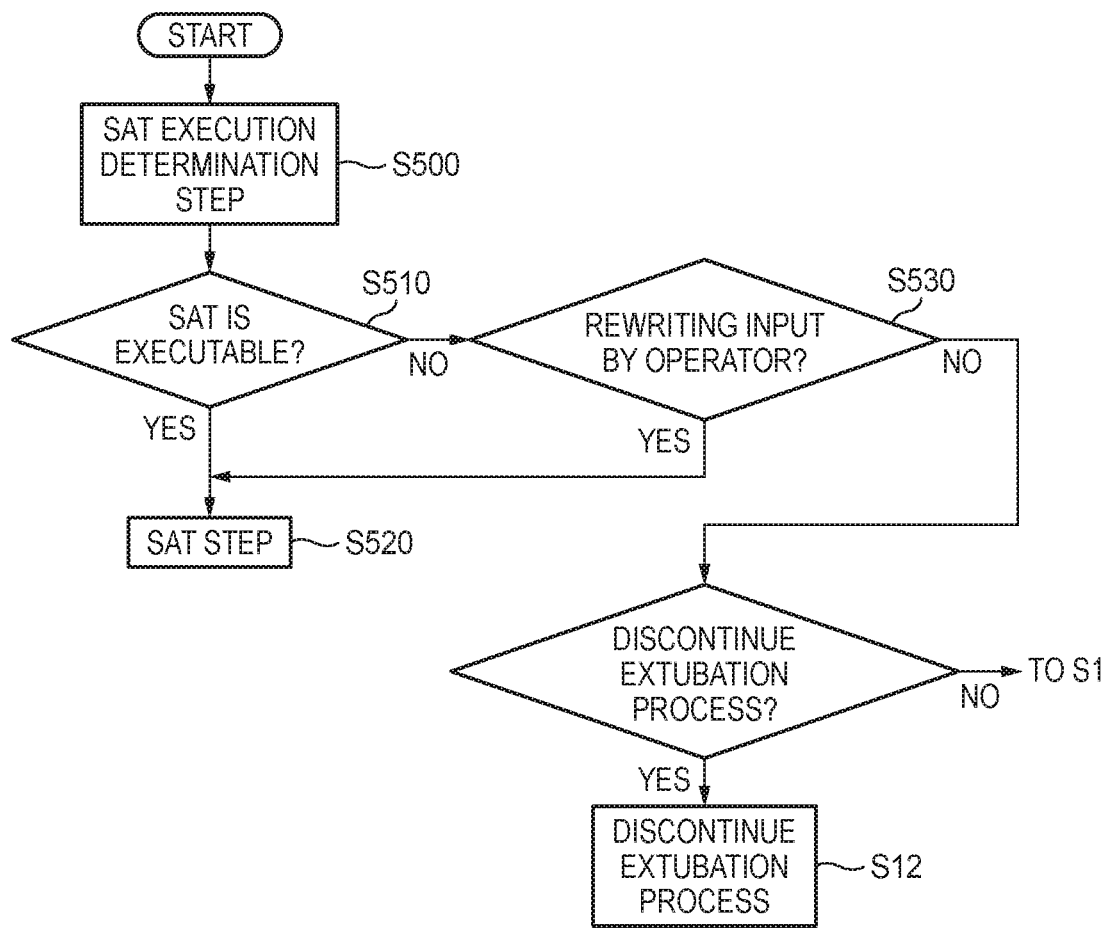
FIG. 13 is a flowchart illustrating a process of rewriting determination results of the SAT execution determination step.

Next, a determination result rewriting process will be described with reference to FIGS. 13 and 14. FIG. 13 shows a flowchart illustrating a process of rewriting determination results of the SAT execution determination step. FIG. 14 shows the extubation process display screen 72 for the SAT execution determination step on which determination results of the SAT execution determination step in which rewriting is performed by an input operation are displayed.

As shown in FIG. 13, the second automatic determining section 38 automatically determines whether the SAT execution determination step (S500) succeeds or fails, based on the result of the SAT execution determination step (S510). If the second automatic determining section 38 determines that SAT is executable (Yes in S510), the determination result of "SAT EXECUTABLE" of the SAT execution determination step is displayed in the step determination result display region 75. Thereafter, the display switching section 33 switches the extubation process display screen 72 for the SAT execution determination step, to the extubation process display screen 72 for an SAT step (see FIG. 15) (S520). On the other hand, if the second automatic determining section 38 determines that SAT is unexecutable (No in S510), the determination result of "SAT UNEXECUTABLE" of the SAT execution determination step is displayed in the step determination result display region 75. Thereafter, if the determination result rewriting section 35 receives the writing input of the operator with respect to the determination result of the SAT execution determination step (Yes in S530), the determination result rewriting section 35 rewrites the determination result of the SAT execution determination step from "SAT UNEXECUTABLE" to "SAT EXECUTABLE" (see FIG. 14). Then, the display switching section 33 switches the extubation process display screen 72 for the SAT execution determination step, to the extubation process display screen 72 for the SAT step (S520). On the other hand, if the determination result rewriting section 35 does not receive the writing input of the operator with respect to the determination result of the SAT execution determination step (No in S530), the process returns to the SAT execution determination step (S1), or the extubation process is discontinued (S512).

As described above, the determination result rewriting section 35 is configured so as to rewrite the determination results of the respective steps (the SAT execution determination step and the like) which are determined by the second automatic determining section 38, in accordance with an input operation of the operator on the input interface section 9. Therefore, the operator can rewrite the determination results of the respective steps in accordance with the situation, and hence the flexibility of the operation of the vital information monitor 1 is improved.

In the case where the determination results of the SAT execution determination step are rewritten by the determination result rewriting section 35 as shown in FIG. 14, moreover, the display mode (the display color or the like) of the determination result of "SAT EXECUTABLE" which is displayed in the step determination result display region 75 may be changed. The determination result rewriting section 35 may be further configured so as to rewrite the determination results which are determined by the first automatic determining section 36.

Moreover, the display switching section 33 is configured so as to switch the extubation process display screen 72 displayed on the displaying section 7, every steps (the SAT execution determination step and the like). Since the extubation process display screen 72 is switched every steps, the operator can easily know the currently executed step. In this way, the operability of the vital information monitor 1 is improved.

Figure 15:
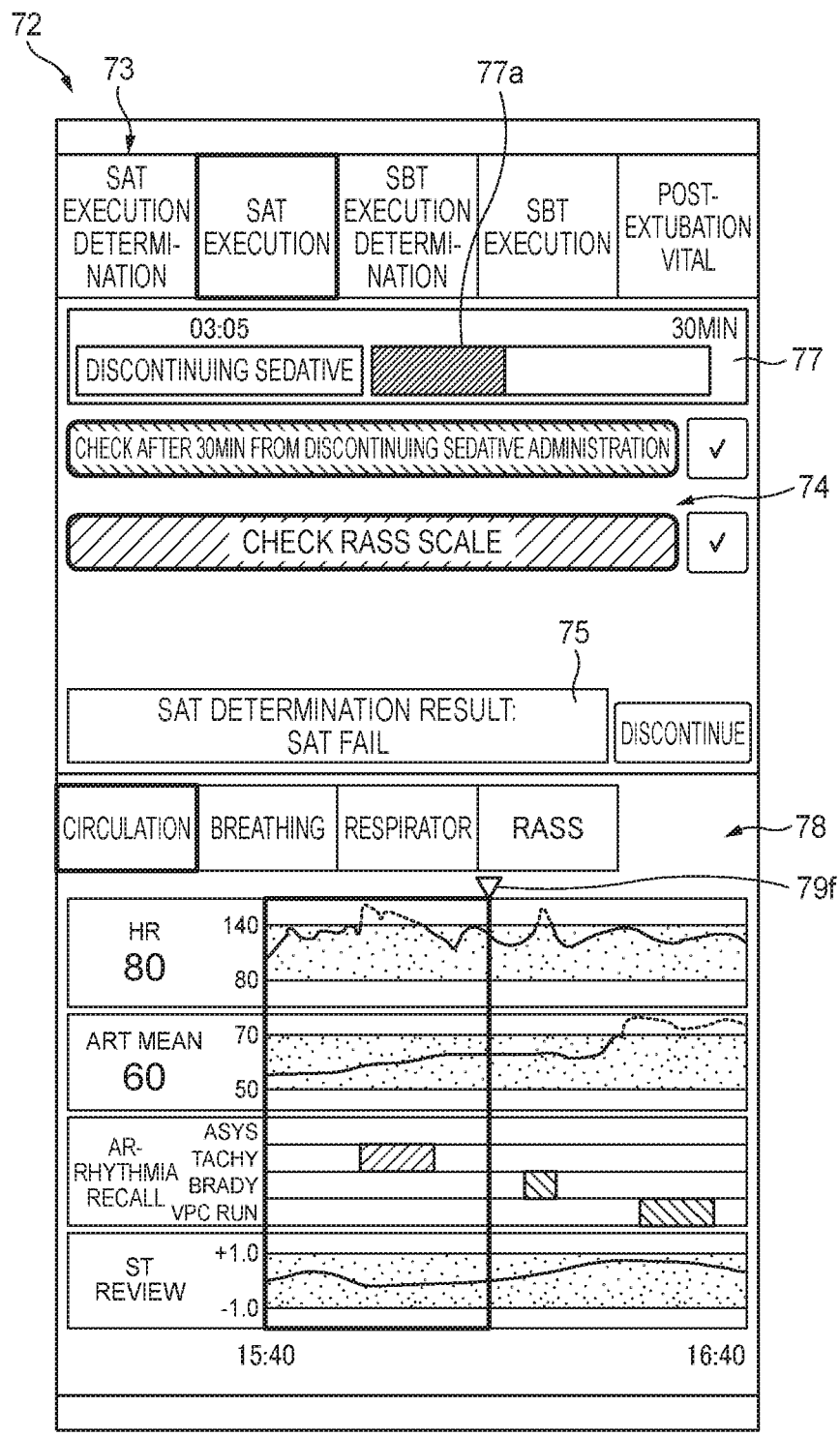
FIG. 15 illustrates an extubation process display screen for an SAT execution step.

Next, the extubation process display screen 72 for the SAT execution step will be briefly described with reference to FIG. 15. FIG. 15 shows the extubation process display screen 72 for the SAT execution step. In the extubation process display screen 72 shown in FIG. 15, the determination items for the SAT execution step have been already determined by the determining section 30, and the success or failure of the SAT execution step (here, the failure of SAT) has been already determined by the second automatic determining section 38.

In the SAT execution step in the embodiment, in order to evaluate whether awakening of the patient is obtained after elapse of a predetermined time period (for example, 30 minutes) from discontinuance of administration of a sedative in the patient, a timer display region 77 is displayed on the extubation process display screen 72. When the time counter 8 of the vital information monitor 1 shown in FIG. 1 counts the elapsed time period, a time scale of an indicator 77a displayed in the timer display region 77 is increased. A pointer 79f indicating the timing when the time counter 8 starts the counting of the elapsed time period may be displayed in the vital sign display region 78.

Figure 16:
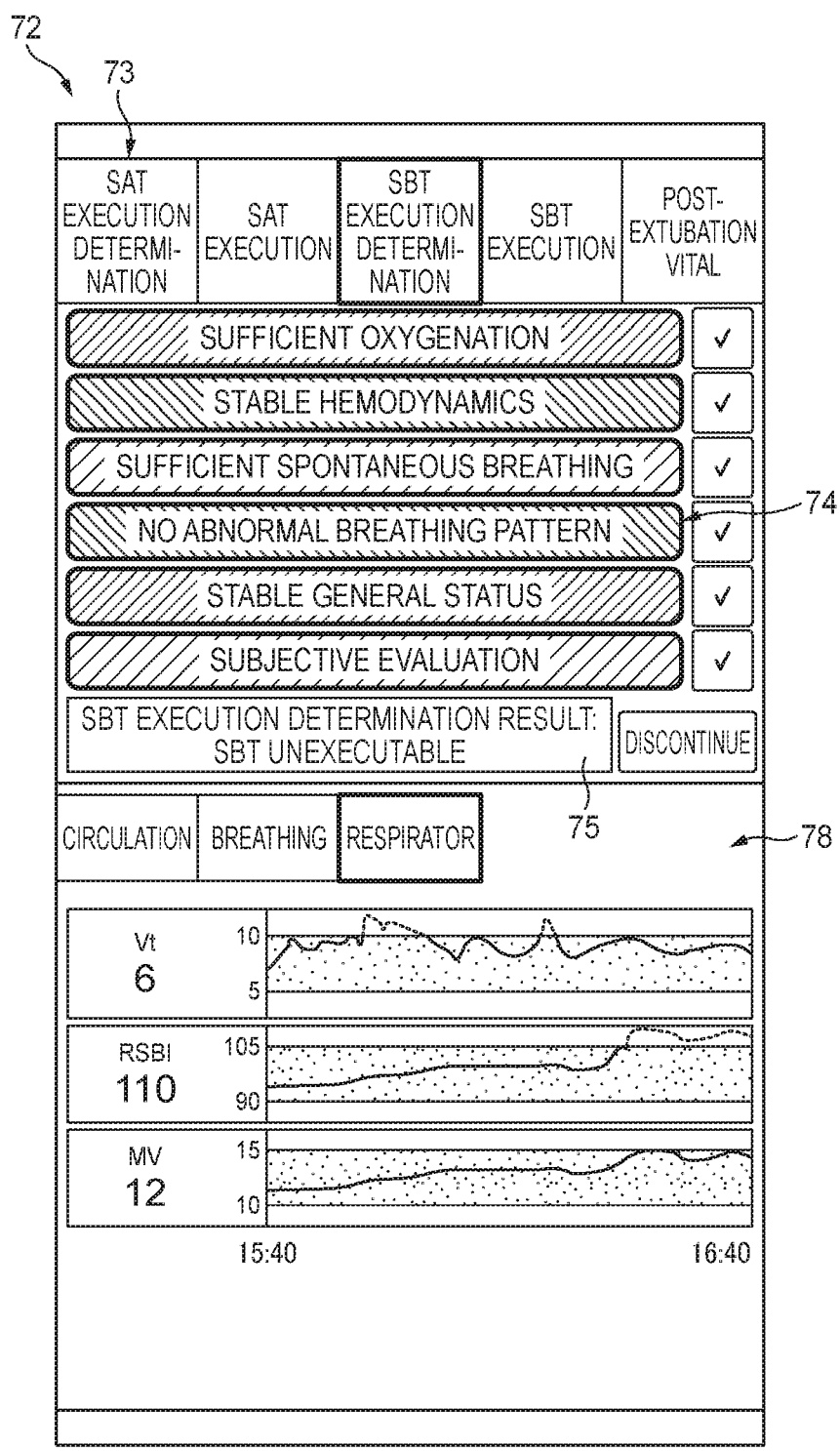
FIG. 16 illustrates an extubation process display screen for an SBT execution determination step.

Next, the extubation process display screen 72 for the SBT execution determination step will be briefly described with reference to FIG. 16. FIG. 16 shows the extubation process display screen 72 for the SBT execution determination step. In the extubation process display screen 72 shown in FIG. 16, the determination items for the SBT execution determination step have been already determined, and the success or failure (here, SBT is unexecutable) of the SBT execution determination step has been already determined by the second automatic determining section 38.

Figure 17:
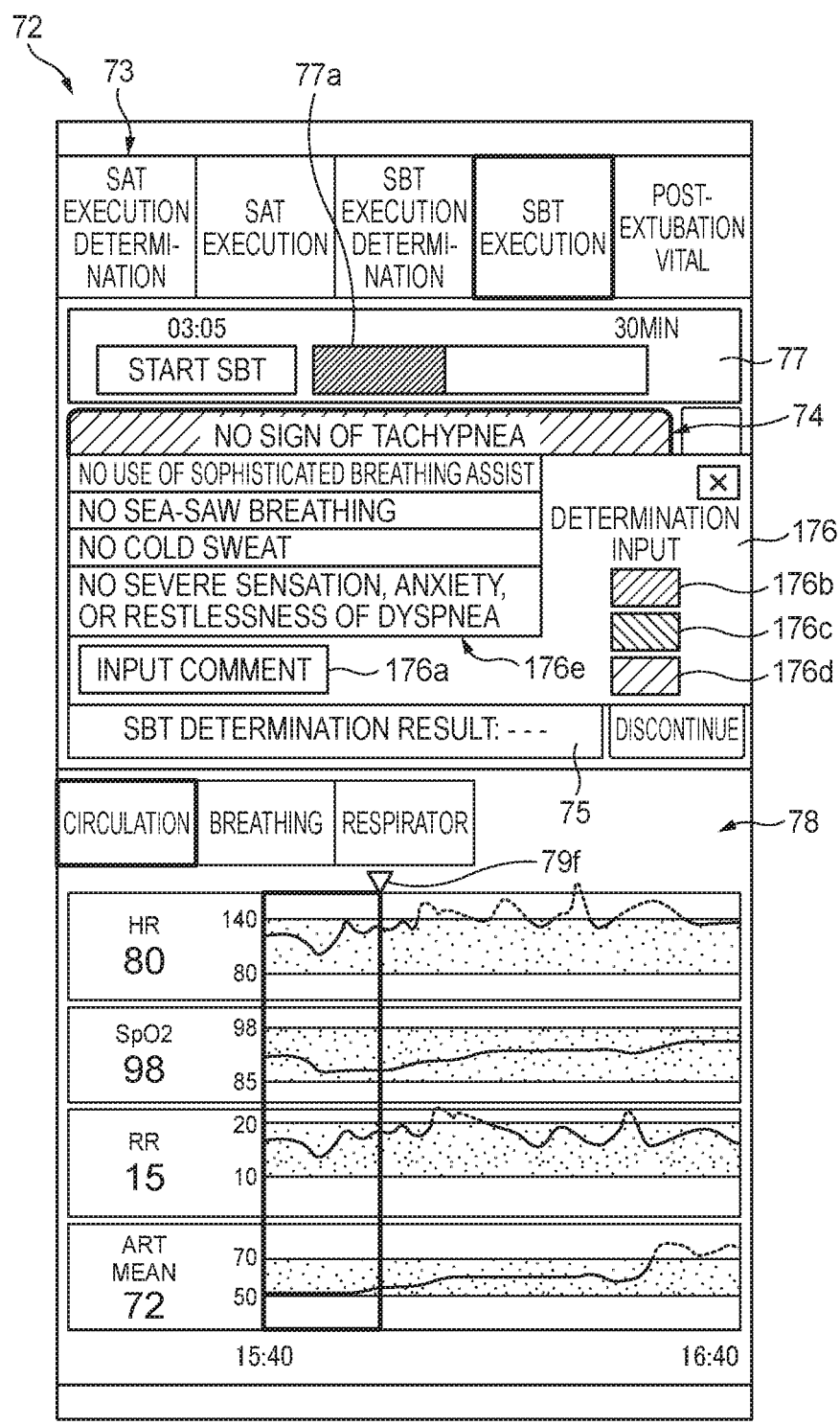
FIG. 17 illustrates an extubation process display screen for an SBT execution step on which an operation input screen for examples of manual determination items is displayed.

Next, the extubation process display screen 72 for the SBT execution step will be briefly described with reference to FIGS. 17 and 18. FIG. 17 shows the extubation process display screen 72 for the SBT execution step. In the extubation process display screen 72 shown in FIG. 18, an "INPUT COMMENT" button 176a, a red determination button 176b, a yellow determination button 176c, a blue determination button 176d, and a condition list 176e for a manual determination item "NO SIGN OF TACHYPNEA" are displayed on an operation input screen 176 on which the operation input screen 176 of this manual determination item is displayed. In accordance with an input operation of the operator on the operation input screen 176, the manual determining section 37 determines whether the manual determination item "NO SIGN OF TACHYPNEA" satisfies conditions described in the condition list 176e or not. In the case where the blue determination button 176b is designated by the operator, for example, the manual determining section 37 determines that the manual determination item satisfies the conditions.

In the SBT execution step in the embodiment, in order to evaluate spontaneous breathing of the patient in a state where the patient is not supported by the respirator 13, the timer display region 77 is displayed on the extubation process display screen 72.

Figure 18:
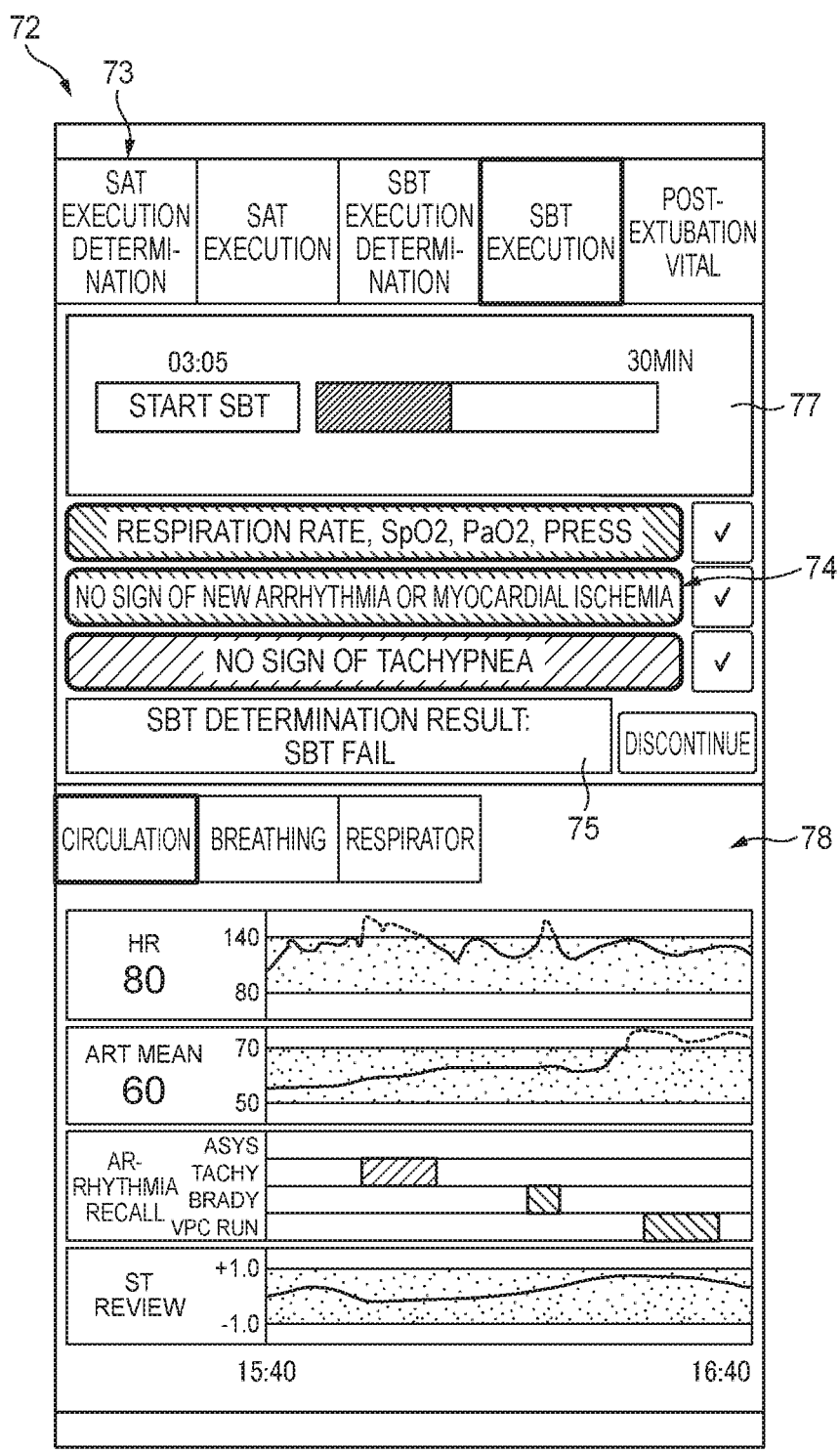
FIG. 18 illustrates the extubation process display screen for the SBT execution step on which determination results of the SBT execution step are displayed.

FIG. 18 shows the extubation process display screen 72 for the SBT execution step on which determination results of the SBT execution determination step are displayed. In the extubation process display screen 72 shown in FIG. 18, the determination items for the SBT execution step have been already determined by the determining section 30, and the success or failure of the SBT execution step (here, the failure of SBT) has been already determined by the second automatic determining section 38.

Next, the extubation process display screen 72 for the post-execution monitoring step will be described. FIG. 19 shows the extubation process display screen 72 for the post-extubation monitoring step on which evaluation items of post-extubation airway obstruction are displayed. FIG. 20 shows the extubation process display screen 72 for the post-extubation monitoring step on which very high-risk group determination items are displayed. FIG. 21 shows the extubation process display screen 72 for the post-extubation monitoring step on which vital signs of a post-extubation patient are displayed. In the extubation process display screen 72 shown in FIG. 21, particularly, various values of vital signs of the post-extubation patient are displayed at intervals of 15 minutes in the upper stage, and various trend waveforms of the vital signs are displayed in the lower stage.

Figure 22:
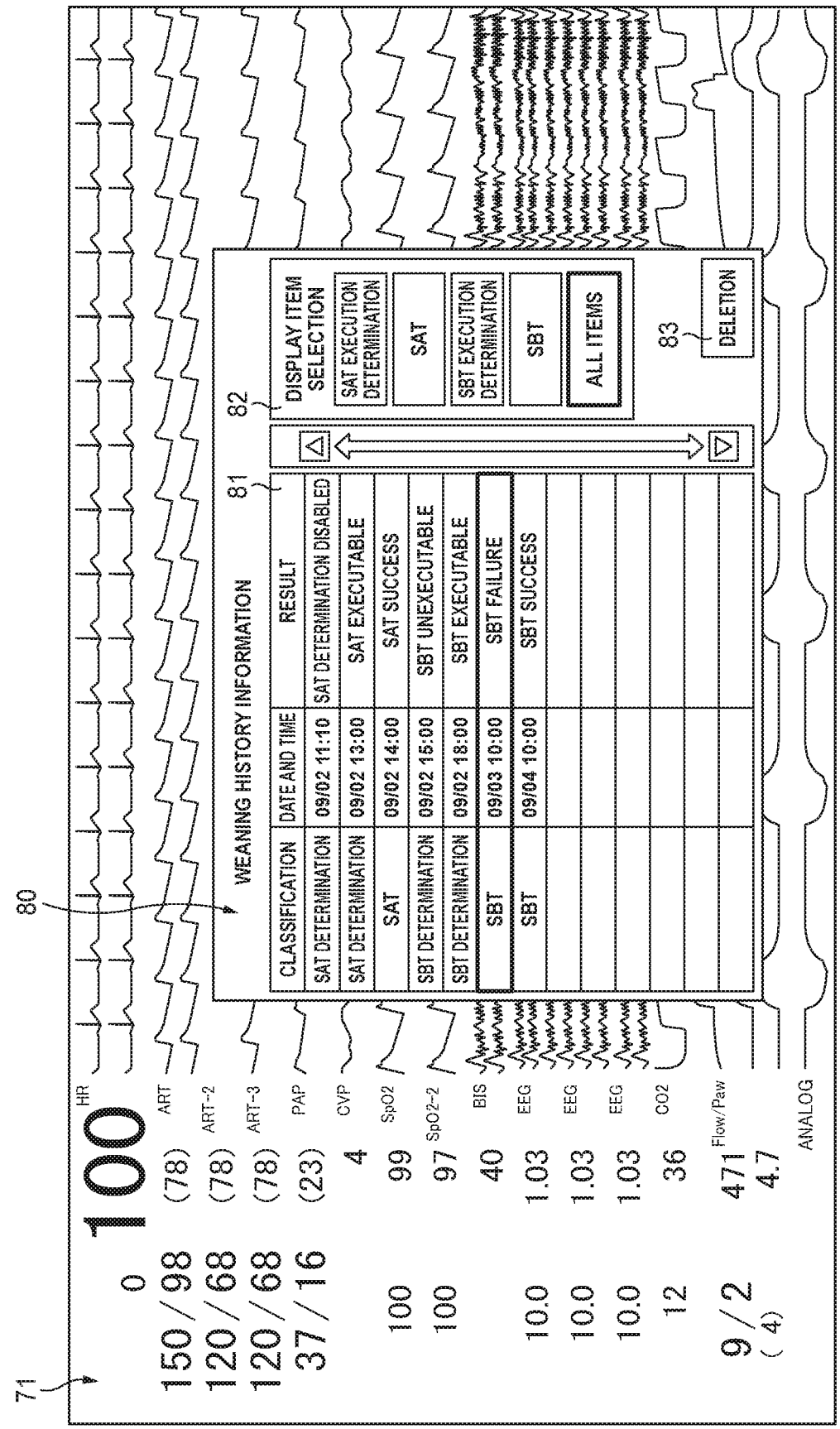
FIG. 22 illustrates a vital sign screen and extubation process history information screen which are displayed on the displaying section of the vital information monitor of the embodiment.

Next, an extubation process history information screen 80 will be described with reference to FIGS. 22 and 23. FIG. 22 shows the vital sign screen 71 and extubation process history information screen 80 which are displayed on the displaying section 7 of the vital information monitor 1. The extubation process history information screen 80 has a history information region 81, a display item selection region 82, and a deletion button 83.

Items showing respective steps which were executed, those showing days and times when the respective steps were executed, and those showing results of the executed steps are displayed in the history information region 81. As shown in FIG. 22, when the operator designates "ALL ITEMS" in the display item selection region 82, history information of all executed steps is displayed in the history information region 81. On the other hand, when the operator designates "SAT EXECUTION DETERMINATION" in the display item selection region 82, only history information with respect to the SAT execution determination step is displayed in the history information region 81.

Figure 23:
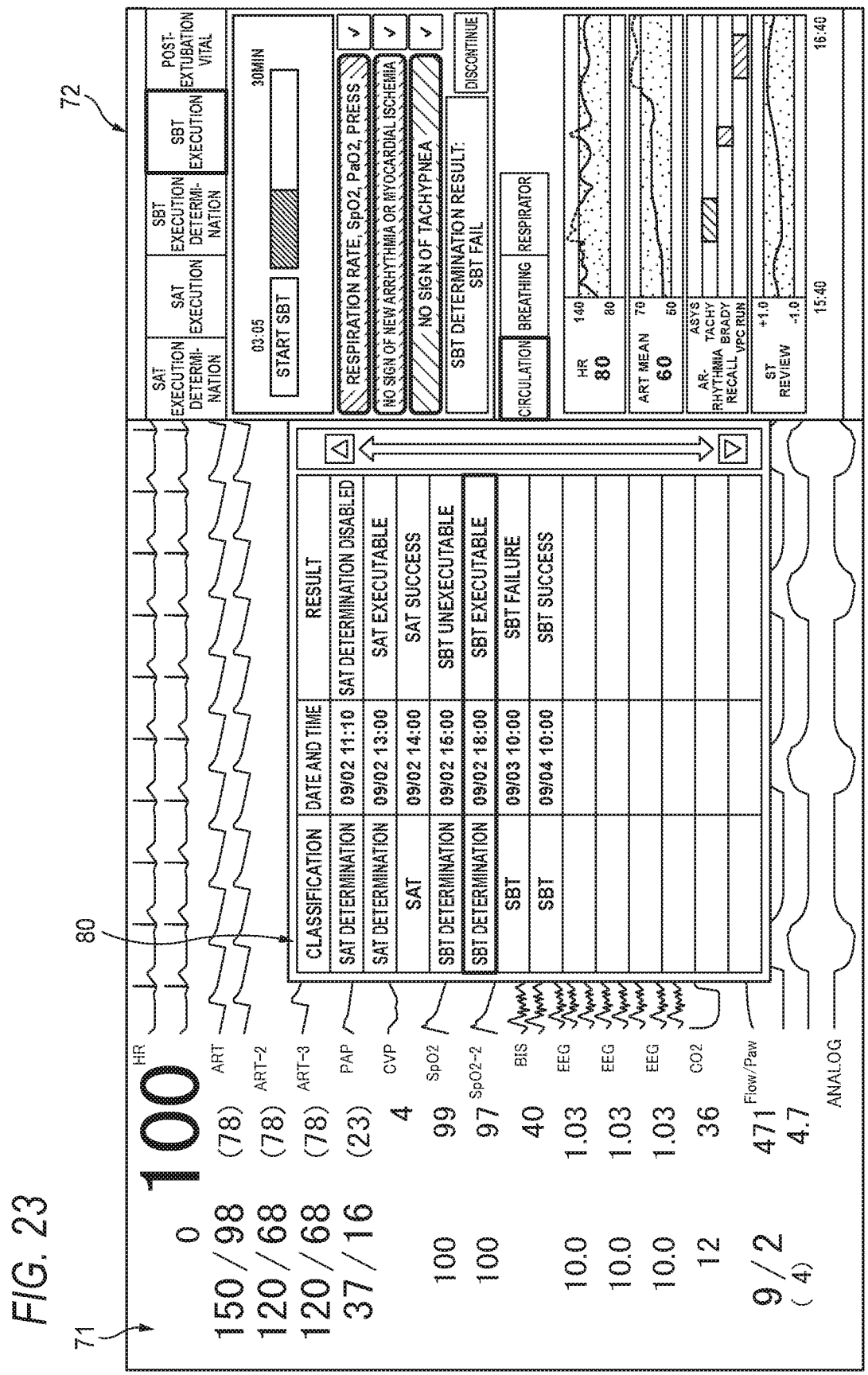
FIG. 23 illustrates a screen on which history information of the SBT execution step is displayed.

When the operator selects the SBT step which was executed at 10 o'clock of September 3, in the history information region 81 as shown in FIG. 22, a detailed screen of the history information of the SBT execution step is displayed on the displaying section 7 as shown in FIG. 23. The detailed screen of the history information corresponds to the extubation process display screen 72 for the SBT execution step shown in FIG. 18.

Moreover, the history information of the extubation process is recorded in the recording section 5. Therefore, the operator is not required to separately input the history information of the extubation process in a computer or the like in each case, and the burden on the operator is reduced. Furthermore, the recorded history information can be used later.

According to the embodiment, the vital signs acquired by the vital sign acquiring section 39, and the extubation process display screen 72 are displayed on the vital information monitor 1, and therefore the medical person can perform the extubation process in accordance with the extubation process display screen 72 while checking the vital signs. As described above, it is possible to provide the vital information monitor 1 which can reduce the burden on a medical person who performs the extubation process based on determination items.

According to the embodiment, moreover, it is possible to provide the vital information monitor 1 which can compatible with the extubation process consisting of the SAT execution determination step, the SAT step, the SBT execution determination step, and the SBT step.

While the embodiment of the invention has been described, the technical scope of the invention should not be limitedly interpreted by the description of the embodiment. It should be understood by those skilled in the art that the embodiment is a mere example, and may be variously changed within the scope of the invention as defined in the claims. The technical scope of the invention should be determined based on the scope of the invention as defined in the claims, and the scope of equivalence thereof.

For example, the extubation process which has been described in the embodiment is a mere example, and the contents of the extubation process can be adequately changed. Although, in the embodiment, the extubation process consisting of the SAT execution determination step, the SAT step, the SBT execution determination step, and the SBT step has been described, particularly, an extubation process consisting of only the SBT execution determination step and the SBT step may be used. It is a matter of course that the technical concept of the invention can be applied also to an extubation process which is entirely different from the extubation process that has been described in the embodiment.

While the extubation process display screen on which the determination items contained in the extubation process are displayed is displayed in the vital information monitor 1 of the embodiment, the technical concept of the invention is not limited to this. That is, the technical concept of the invention can be applied also to a vital information monitor for displaying a diagnosis process display screen on which determination items contained in a diagnosis process for diagnosing the patient are displayed. Also in this case, while observing vital signs, the medical person can diagnose the patient in accordance with the diagnosis process display screen. In this way, it is possible to provide a vital information monitor which can reduce the burden on a medical person who performs a diagnosis based on determination items. The diagnosis process which is referred here includes all diagnosis processes for diagnosing the patient.

The summary of the above-described embodiment will be described.

According to an aspect of the embodiment, a vital information monitor includes a vital sign acquiring section which acquires vital signs of a patient into whom a tracheal tube connected to a respirator is intubated, a producing section which produces an extubation process display screen on which determination items contained in an extubation process for removing the tracheal tube from the patient are displayed, a displaying section on which the vital signs acquired by the vital sign acquiring section and the extubation process display screen are displayed, and a determining section which determines whether the determination items satisfy predetermined conditions.

With this configuration, the vital signs acquired by the vital sign acquiring section and the extubation process display screen are displayed on the vital information monitor, and therefore a medical person can perform the extubation process in accordance with the extubation process display screen, while observing the vital signs. Therefore, it is possible to provide a vital information monitor which can reduce a burden on the medical person performing the extubation process based on the determination items.

The vital information monitor may further include a display changing section which, after the determination has been carried out on the determination items, changes display modes of the determination items.

With this configuration, the display modes of the determined determination items are changed, and therefore the medical person can visually recognize which determination items have been already determined. Consequently, it is possible to prevent an erroneous extubation process from being executed, and the operability of the vital information monitor is improved.

The display changing section may change the display modes of the determination items in accordance with determination results of the determination items.

With this configuration, the display modes of the determination items are changed in accordance with the determination results, and therefore the medical person can visually recognize which determination items satisfy the predetermined conditions. Consequently, it is possible to prevent an erroneous extubation process from being executed, and the operability of the vital information monitor is improved.

The display changing section may change display colors of the determination items in accordance with the determination results of the determination items.

With this configuration, the display colors of the determination items are changed in accordance with the determination results, and therefore the medical person can visually recognize which determination items satisfy the predetermined conditions or not. Consequently, it is possible to prevent an erroneous extubation process from being executed, and the operability of the vital information monitor is improved.

The vital information monitor may further include an input interface section which receives an input operation of an operator, and a condition changing section which changes the predetermined conditions in accordance with an input operation that is performed by the operator on the input interface section.

With this configuration, the medical person can change the conditions of the determination items, and therefore optimum determination items can be set according to the condition of the patient.

The vital information monitor may further include a recording section which records the determination items and determination results of the determination items.

With this configuration, history information of the extubation process such as determination results is recorded. Therefore, the medical person is not required to separately input the history information of the extubation process in a computer or the like in each case, and the burden on the medical person is further reduced. Moreover, the recorded history information can be used later.

The extubation process display screen may include a determination item display region where the determination items are displayed, and a vital sign display region where a part of the vital signs acquired by the vital sign acquiring section is displayed.

With this configuration, while observing the partial vital signs displayed in the vital sign display region of the extubation process display screen, the medical person can perform the extubation process in accordance with the determination item display region of the extubation process display screen. In this way, the operability of the vital information monitor is improved.

The vital information monitor may further include an input interface section which receives an input operation of an operator. The determination items may have an automatic determination item and a manual determination item. The determining section may include a first automatic determining section which automatically determines whether the automatic determination item satisfies predetermined conditions, based on the vital signs, and a manual determining section which determines whether the manual determination item satisfies predetermined conditions, in accordance with an input operation of the operator on the input interface section.

With this configuration, it is possible to provide a vital information monitor which includes a manual determination item that is manually determined based on a subjective view of the medical person, and an automatic determination item that is automatically determined based on vital signs.

The extubation process may have a plurality of steps. The vital information monitor may further include a display switching section which switches the extubation process display screen that is displayed on the displaying section, in each of the steps.

With this configuration, the extubation process display screen is switched in each step, and therefore the medical person can easily know which step is currently performed. In this way, the operability of the vital information monitor is improved.

Each of the steps may have a plurality of determination items. The vital information monitor may further include a second automatic determining section which automatically determines a success or failure of each of the steps in accordance with determination results of the plurality of determination results of each step.

With this configuration, the success or failure of each step is automatically determined. In this way, the medical person determines whether the process may proceed to the next step or not, based on the automatic determination, and therefore it is possible to prevent an erroneous extubation process from being executed.

The vital information monitor may further include a determination result rewriting section which rewrites the determination results that are determined by the second automatic determining section, in accordance with an input operation of the operator on the input interface section.

With this configuration, the determination results that are determined by the second automatic determining section can be rewritten by an input operation of the operator. In this way, the automatic determination results can be rewritten in accordance with the situation, and therefore the flexibility of the operation of the vital information monitor is improved.

The extubation process may include a step of determining whether a transfer can be made to a support minimum state where at least support by the respirator for breathing of the patient is minimum, or an unsupported state where support by the respirator for breathing of the patient is not performed (hereinafter, SBT execution determination step), and a step of evaluating spontaneous breathing of the patient in the support minimum state or the unsupported state (hereinafter, SBT execution step).

With this configuration, it is possible to provide a vital information monitor which can compatible with the SBT execution determination step, and the SBT execution step.

The extubation process may further include a step of determining whether administration of a sedative in the patient can be discontinued, or whether an amount of a sedative to be administered to the patient can be reduced (hereinafter, SAT execution determination step), and a step of evaluating whether awakening of the patient is attained in a state where administration of the sedative in the patient is discontinued or where the amount of the sedative to be administered to the patient is reduced (hereinafter, SAT execution step).

With this configuration, it is possible to provide a vital information monitor which can compatible with the SBT execution determination step, the SBT execution step, the SAT execution determination step, and the SAT execution step.

According to another aspect of the embodiment, a vital information monitor includes a vital sign acquiring section which acquires vital signs of a patient, an input interface section which receives an input of an operator, a producing section which produces a diagnosis process display screen on which determination items contained in a diagnosis process for diagnosing the patient are displayed, a displaying section on which the vital signs acquired by the vital sign acquiring section and the diagnosis process display screen are displayed, a determining section which determines whether the determination items satisfy predetermined conditions, a recording section which records the determination items and determination results of the determination items, and a display changing section which, after the determination has been made on the determination items, changes display modes of the determination items.

With this configuration, vital signs acquired by the vital sign acquiring section, and the diagnosis process display screen are displayed on the vital information monitor, and therefore the medical person can perform diagnosis in accordance with the diagnosis process display screen, while observing the vital signs. Therefore, it is possible to provide a vital information monitor which can reduce the burden on a medical person who performs diagnosis based on determination items.

This application incorporates the content disclosed in Japanese Patent Application (No. 2015-085133) filed on Apr. 17, 2015 as appropriate.

The invention claimed is:

1. A vital information monitor comprises:
   a vital sign acquiring section which acquires vital signs of a patient into whom a tracheal tube connected to a respirator is intubated;
   a producing section which produces an extubation process display screen on which determination items contained in an extubation process for removing the tracheal tube from the patient are displayed;
   a displaying section on which the vital signs acquired by the vital sign acquiring section and the extubation process display screen are displayed;
   a determining section which determines whether the determination items satisfy predetermined conditions,
   wherein the extubation process includes a plurality of steps,
   wherein the vital information monitor further comprises a display switching section which switches the extubation process display screen that is displayed on the displaying section, in each of the steps,
   wherein each of the steps has a plurality of determination items, and
   wherein the vital information monitor further comprises a second automatic determining section which automatically determines a success or failure of each of the steps in accordance with determination results of the plurality of determination results of each step.

2. The vital information monitor according to claim 1, further comprising a display changing section which, after the determination has been carried out on the determination items, changes display modes of the determination items.

3. The vital information monitor according to claim 2, wherein the display changing section changes the display modes of the determination items in accordance with determination results of the determination items.

4. The vital information monitor according to claim 3, wherein the display changing section changes display colors of the determination items in accordance with the determination results of the determination items.

5. The vital information monitor according to claim 1, further comprising:
   an input interface section which receives an input operation of an operator; and
   a condition changing section which changes the predetermined conditions in accordance with an input operation that is performed by the operator on the input interface section.

6. The vital information monitor according to claim 1, further comprising a recording section which records the determination items and determination results of the determination items.

7. The vital information monitor according to claim 1, wherein the extubation process display screen includes a determination item display region where the determination items are displayed, and a vital sign display region where a part of the vital signs acquired by the vital sign acquiring section is displayed.

8. The vital information monitor according to claim 1, further comprising an input interface section which receives an input operation of an operator,
   wherein the determination items include an automatic determination item and a manual determination item, and
   wherein the determining section comprises:
      a first automatic determining section which automatically determines whether the automatic determination item satisfies predetermined conditions, based on the vital signs; and
      a manual determining section which determines whether the manual determination item satisfies predetermined conditions, in accordance with an input operation of the operator on the input interface section.

9. The vital information monitor according to claim 1, further comprising a determination result rewriting section which rewrites the determination results that are determined by the second automatic determining section, in accordance with an input operation of the operator on the input interface section.

10. The vital information monitor according to claim 1, wherein the extubation process includes a step of determining whether a transfer can be made to a support minimum state where at least support by the respirator for breathing of the patient is minimum, or an unsupported state where support by the respirator for breathing of the patient is not performed, and a step of evaluating spontaneous breathing of the patient in the support minimum state or the unsupported state.

11. The vital information monitor according to claim 10, wherein the extubation process further include a step of determining whether administration of a sedative in the patient can be discontinued, or whether an amount of a sedative to be administered to the patient can be reduced, and a step of evaluating whether awakening of the patient is attained in a state where administration of the sedative in the patient is discontinued or where the amount of the sedative to be administered to the patient is reduced.

12. The vital information monitor according to claim 1, further comprising:

an input interface section which receives an input of an operator;
a recording section; and
a display changing section,
wherein the producing section is configured to produce a diagnosis process display screen on which determination items contained in a diagnosis process for diagnosing the patient are displayed;
wherein the displaying section is configured to display the vital signs acquired by the vital sign acquiring section and the diagnosis process display screen;
wherein the determining section is configured to determine whether the determination items contained in the diagnosis process satisfy predetermined conditions;
wherein the recording section is configured to record the determination items and determination results of the determination items; and
wherein the display changing section is configured to change display modes of the determination items after the determination has been made on the determination items.

\* \* \* \* \*